United States Patent
Brar et al.

(10) Patent No.: US 12,369,982 B2
(45) Date of Patent: *Jul. 29, 2025

(54) SELECTION OF HYPERTENSIVE PATIENTS FOR TREATMENT WITH RENAL DENERVATION

(71) Applicant: Medtronic Ireland Manufacturing Unlimited Company, Dublin (IE)

(72) Inventors: Sandeep Brar, Dublin, CA (US); Martin Fahy, Brooklyn, NY (US); Vanessa Debruin, Lake Elmo, MN (US); Colleen Gilbert, Tallahassee, FL (US)

(73) Assignee: Medtronic Ireland Manufacturing Unlimited Company, Dublin (IE)

(*) Notice: Subject to any disclaimer, the term of this patent is extended or adjusted under 35 U.S.C. 154(b) by 274 days.

This patent is subject to a terminal disclaimer.

(21) Appl. No.: 18/166,325

(22) Filed: Feb. 8, 2023

(65) Prior Publication Data

US 2023/0190381 A1 Jun. 22, 2023

Related U.S. Application Data

(63) Continuation of application No. 16/877,327, filed on May 18, 2020, now Pat. No. 11,607,275.

(Continued)

(51) Int. Cl.
*A61B 34/10* (2016.01)
*A61B 18/02* (2006.01)
(Continued)

(52) U.S. Cl.
CPC .............. *A61B 34/10* (2016.02); *A61B 18/02* (2013.01); *A61B 18/06* (2013.01);
(Continued)

(58) Field of Classification Search
CPC ... A61B 17/32002; A61B 18/02; A61B 18/06; A61B 18/1492; A61B 2017/320069;
(Continued)

(56) References Cited

U.S. PATENT DOCUMENTS 9,855,317 B2 * 1/2018 Bright ..................... A61P 29/02
10,111,708 B2   10/2018 Wang
(Continued)

FOREIGN PATENT DOCUMENTS

CN   102949176 A   3/2013
CN   103796604 A   5/2014
(Continued)

OTHER PUBLICATIONS

Shen et al., "Preliminary Research of Diagnosis and Therapy of Neurogenic Orthostatic Hypotension: A New Attempt", China Doctor Dissertations Full-text Database Medicine and Health Science and Technology Series, May 1, 2013, 177 pp., Translation provided for only the Abstract.

(Continued)

*Primary Examiner* — George Manuel
(74) *Attorney, Agent, or Firm* — Shumaker & Sieffert, P.A.

(57) ABSTRACT

Methods, systems, devices, assemblies and apparatuses for treatment of hypertension in a patient using renal denervation. The therapeutic assembly includes an energy delivery element. The energy delivery element is configured to provide renal denervation energy to a nerve within a blood vessel of a patient. The therapeutic assembly includes a controller. The controller is coupled to the energy delivery element. The controller is configured to determine that the hypertension in the patient is orthostatic. The controller is configured to apply renal denervation energy to the patient using the energy delivery element.

20 Claims, 22 Drawing Sheets

Related U.S. Application Data

(60) Provisional application No. 62/850,195, filed on May 20, 2019.

(51) Int. Cl.
| | |
|---|---|
| *A61B 18/06* | (2006.01) |
| *A61B 18/14* | (2006.01) |
| *G16H 50/20* | (2018.01) |
| *A61B 5/0205* | (2006.01) |
| *A61B 5/021* | (2006.01) |
| *A61B 5/11* | (2006.01) |
| *A61B 17/32* | (2006.01) |
| *A61B 18/00* | (2006.01) |
| *A61B 34/00* | (2016.01) |

(52) U.S. Cl.
CPC ......... *A61B 18/1492* (2013.01); *G16H 50/20* (2018.01); *A61B 5/0205* (2013.01); *A61B 5/021* (2013.01); *A61B 5/1116* (2013.01); *A61B 17/32002* (2013.01); *A61B 2017/320069* (2017.08); *A61B 2018/00345* (2013.01); *A61B 2018/00434* (2013.01); *A61B 2018/00511* (2013.01); *A61B 2018/00577* (2013.01); *A61B 2018/00994* (2013.01); *A61B 2018/0212* (2013.01); *A61B 2034/104* (2016.02); *A61B 2034/256* (2016.02)

(58) Field of Classification Search
CPC ........... A61B 2018/00345; A61B 2018/00404; A61B 2018/00434; A61B 2018/00511; A61B 2018/00577; A61B 2018/00791; A61B 2018/00875; A61B 2018/00994; A61B 2018/0212; A61B 2018/1467; A61B 2018/1861; A61B 2034/104; A61B 2034/256; A61B 2090/3966; A61B 2505/05; A61B 2560/029; A61B 34/10; A61B 34/25; A61B 5/0077; A61B 5/0205; A61B 5/02055; A61B 5/021; A61B 5/022; A61B 5/1116; A61B 5/201; A61B 5/4836; A61B 5/4893; A61B 5/6855; A61B 5/7475; A61B 90/98; A61N 2007/0043; G16H 20/30; G16H 40/63; G16H 50/20

See application file for complete search history.

(56) References Cited

U.S. PATENT DOCUMENTS

| | | |
|---|---|---|
| 10,194,979 B1 | 2/2019 | Brar et al. |
| 10,413,709 B2 | 9/2019 | Jamous et al. |
| 11,234,762 B2 | 2/2022 | Cheng et al. |
| 2008/0200819 A1 | 8/2008 | Lynn et al. |
| 2014/0275993 A1 | 9/2014 | Ballakur |
| 2018/0368914 A1 | 12/2018 | Cheng et al. |

FOREIGN PATENT DOCUMENTS

| | | |
|---|---|---|
| CN | 107802341 A | 3/2018 |
| CN | 107811703 A | 3/2018 |
| CN | 108601613 A | 9/2018 |
| CN | 109475724 A | 3/2019 |
| EP | 3028628 A1 | 6/2016 |
| WO | 2012015720 A1 | 2/2012 |
| WO | 2015085119 A1 | 6/2015 |
| WO | 2016025323 A1 | 2/2016 |
| WO | 2017156039 A1 | 9/2017 |

OTHER PUBLICATIONS

Zhou et al., "Preliminary Study on the Effect of Blood Pressure of Transabdominal Radiofrequency Renal Denervation via Adventitia in Beagle Dog Model", Chinese Master's Theses Full-text Database Medicine and Health Science and Technology Series, Soochow University, May 2016, 55 pp., (Applicant points out, in accordance with MPEP 609.04(a), that the year of publication, 2016, is sufficiently earlier than the effective U.S. filing date, so that the particular month of publication is not an issue.) Translation provided for only the Abstract.

Gisbertz et al., "Renal sympathetic denervation significantly reduces blood pressure but not cause orthostatic dysregulation in patients with resistant hypertension", Congress of the European-Society-of-Cardiology, vol. 34, No. 1, Aug. 1, 2013, 2 pp.

* cited by examiner

OFF MED-INTERACTION TESTS

Definition 1: SBP change from Supine to Standing >=20 OR DBP change >=10

| 24-hour SBP Change at 3-Months | DF | Type III SS | Mean Square | F Value | Pr > F |
|---|---|---|---|---|---|
| Baseline 24-hr SBP | 1 | 646.7335101 | 646.7335101 | 7.12 | 0.0096 |
| Treatment (RDN/Control) | 1 | 636.2769015 | 636.2769015 | 7.01 | 0.0101 |
| Orthostatic Htn (y/N) | 1 | 174.4608736 | 174.4608736 | 1.92 | 0.1703 |
| Treatment x Orthostatic HTN Interaction | 1 | 325.2558063 | 325.2558063 | 3.58 | 0.0628 |

| Office SBP Change at 3-Months | DF | Type III SS | Mean Square | F Value | Pr > F |
|---|---|---|---|---|---|
| Baseline Office SBP | 1 | 937.1891519 | 937.1891519 | 5.14 | 0.0263 |
| Treatment (RDN/Control) | 1 | 964.8453979 | 964.8453979 | 5.29 | 0.0243 |
| Orthostatic Htn (y/N) | 1 | 57.3293056 | 57.3293056 | 0.31 | 0.5767 |
| Treatment x Orthostatic HTN Interaction | 1 | 1.1266305 | 1.1266305 | 0.01 | 0.9376 |

FIG. 13

OFF MED - 3M RESPONDER ANALYSIS (DEF 1)
RDN ARM ONLY

| Orthostatic HTN Definition 1 | Orthostatic HTN: YES | Orthostatic HTN: NO | P-Value |
|---|---|---|---|
| 24-hour SBP Change @ 3M ≤ -10 mmHg | 90% (9/10) | 20.0% (5/25) | <0.001 |
| Morning (7am-9am) SBP Change @ 3M ≤ -10 mmHg | 60% (6/10) | 44% (11/25) | 0.471 |
| Moving Peak Morning (6am-10am) SBP Change @ 3M ≤ -10 mmHg | 55.6% (5/9) | 52.4% (11/21) | 0.306 |
| Nighttime (1am-6am) SBP Change @ 3M ≤ -10 mmHg | 60% (6/10) | 24% (6/25) | 0.059 |
| Daytime (9am-9pm) SBP Change @ 3M ≤ -10 mmHg | 90% (9/10) | 24% (6/25) | <0.001 |

FIG. 14

OFF MED-INTERACTION TESTS

Definition 2: SBP change from Supine to Standing >=10 OR DBP change >=10

| 24-hour SBP Change at 3-Months | DF | Type III SS | Mean Square | F Value | Pr > F |
|---|---|---|---|---|---|
| Baseline 24-hr SBP | 1 | 682.8098977 | 682.8098977 | 7.54 | 0.0078 |
| Treatment (RDN/Control) | 1 | 520.1874108 | 520.1874108 | 5.74 | 0.0194 |
| Orthostatic Htn (y/N) | 1 | 257.7055169 | 257.7055169 | 2.84 | 0.0964 |
| Treatment x Orthostatic HTN Interaction | 1 | 229.1458719 | 229.1458719 | 2.53 | 0.1165 |

| Office SBP Change at 3-Months | DF | Type III SS | Mean Square | F Value | Pr > F |
|---|---|---|---|---|---|
| Baseline Office SBP | 1 | 1034.45453 | 1034.45453 | 5.66 | 0.02 |
| Treatment (RDN/Control) | 1 | 997.373047 | 997.373047 | 5.45 | 0.0223 |
| Orthostatic Htn (y/N) | 1 | 0.830466 | 0.830466 | 0 | 0.9465 |
| Treatment x Orthostatic HTN Interaction | 1 | 15.211591 | 15.211591 | 0.08 | 0.7739 |

FIG. 20

OFF MED - 3M RESPONDER ANALYSIS (DEF 2)
RDN ARM ONLY

| Orthostatic HTN Definition 2 | Orthostatic HTN: YES | Orthostatic HTN: NO | P-Value |
|---|---|---|---|
| 24-hour SBP Change @ 3M ≤ -10 mmHg | 76.9% (10/13) | 18.2% (4/22) | 0.001 |
| Morning (7am-9am) SBP Change @ 3M ≤ -10 mmHg | 53.8% (7/13) | 45.5% (10/22) | 0.733 |
| Moving Peak Morning (6am-10am) SBP Change @ 3M ≤ -10 mmHg | 50% (6/12) | 55.6% (10/18) | 0.999 |
| Nighttime (1am-6am) SBP Change @ 3M ≤ -10 mmHg | 53.8% (7/13) | 22.7% (5/22) | 0.079 |
| Daytime (9am-9pm) SBP Change @ 3M ≤ -10 mmHg | 76.9% (10/13) | 22.7% (5/22) | 0.004 |

FIG. 21

SELECTION OF HYPERTENSIVE PATIENTS FOR TREATMENT WITH RENAL DENERVATION

PRIORITY CLAIM

This application is a continuation application of U.S. patent application Ser. No. 16/877,327 filed on May 18, 2020, and titled, "SELECTION OF HYPERTENSIVE PATIENTS FOR TREATMENT WITH RENAL DENERVATION," which claims priority to and the benefit of U.S. Provisional Application No. 62/850,195, titled, "METHOD FOR SELECTION OF HYPERTENSIVE PATIENTS FOR TREATMENT WITH RENAL DENERVATION," and filed on May 20, 2019. Each of the aforementioned priority applications is hereby incorporated by reference in their entireties.

BACKGROUND

1. Field

This specification relates to a system, a device, a method and/or an apparatus for determining and selecting hypertensive patients that are responsive to treatment with renal denervation.

2. Description of the Related Art

Various non-invasive approaches have been developed to perform renal sympathetic denervation (RDN) procedures for the reduction of high blood pressure (BP) in patients at risk for cardiovascular complications and death due to inadequate control of their hypertension. Renal denervation is a minimally invasive procedure to treat resistant hypertension. During renal denervation, a nurse, doctor, technician or other hospital staff (or "clinician") uses stimuli or energy, such as radiofrequency, ultrasound, cooling or other energy, to perform ablation within the renal arteries. This reduces activity of the nerves surrounding the vessel, which has been shown to result in a decrease in blood pressure and other benefits. The clinician uses the renal denervation device to deliver the stimuli or energy to the treatment site, e.g., through one or more electrodes of the renal denervation device. The stimuli at the treatment site may pass through the wall of the blood vessel, which may result in various resultant RDN-related depressor effects. The resultant RDN-related depressor effects include efferent sympathetic nerve ablation causing decrease in nocturnal BP, and afferent sympathetic nerve ablation, resulting in the central sympatholytic activity causing decrease in daytime BP. Not all patients with refractory or resistant hypertension, however, may benefit from RDN. Therefore, it is useful to identify patients whom likely benefit from a renal denervation procedure.

Additionally, it is important to understand the patient's response to the stimuli in order to determine the best and most effective course of treatment to administer to predict the overall effectiveness of the administered treatment on the patient. This allows the doctor, nurse or other healthcare professional to adjust, modify and/or otherwise monitor and control the treatment to provide for effective treatment and determine a likelihood of success of the course of treatment. Thus, the selection of patients and the determination of treatment for the patient is important to provide and administer effective treatment.

Accordingly, there is a need for a system, apparatus and/or method to manage, adjust or otherwise control the selection of patients and to administer treatment including the delivery of renal denervation energy to provide for effective treatment that accurately mirrors the anticipated result on a parameter of the patient or a disease condition.

SUMMARY

In general, one aspect of the subject matter described in this specification is embodied in a method for treatment of hypertension in a patient. The method includes determining that hypertension in the patient is orthostatic. The method includes applying renal denervation energy to the patient.

These and other embodiments may optionally include one or more of the following features. The method may include measuring a baseline standing systolic blood pressure (SBP) of the patient. The method may include measuring a baseline supine SBP of the patient. The method may include determining that the baseline standing systolic blood pressure (SBP) of the patient is greater than the baseline supine SBP by at least 20 mmHg to determine that the hypertension in the patient is orthostatic. The method may include determining that the baseline standing systolic blood pressure (SBP) of the patient is greater than the baseline supine SBP by at least 10 mmHg to determine that the hypertension in the patient is orthostatic.

The method may include obtaining user input that indicates the baseline standing systolic blood pressure (SBP), the baseline supine systolic blood pressure (SBP), the baseline standing diastolic blood pressure (DBP) and the baseline supine diastolic blood pressure (DBP). The method may include measuring a baseline standing diastolic blood pressure (DBP) of the patient. The method may include measuring a baseline supine DBP of the patient. The method may include determining that the baseline standing diastolic blood pressure (DBP) of the patient is greater than the baseline supine DBP by at least 10 mmHg.

The method may include determining a number of ablations based on the determination that the hypertension in the patient is orthostatic. The method may include applying the renal denervation energy or choosing not to consider a patient for renal denervation. The application of the renal denervation energy may be based on the number of ablations and the amount of energy to be delivered in each ablation. The method may include applying the renal denervation energy endovascularly, intravascularly or externally. The method may include applying the renal denervation energy to the patient using at least one of using radio frequency (RF) ablation, chemicals, cryotherapy or ultrasound.

The method may include determining that the patient is in a supine position. The method may include measuring a supine blood pressure of the patient when the patient is in the supine position. The method may include waiting a period of time before measuring a standing blood pressure. The method may include determining that the patient is in a standing position. The method may include measuring a standing blood pressure of the patient when the patient in the standing position. The method may include comparing the supine blood pressure to the standing blood pressure to determine whether the hypertension in the patient is orthostatic. The method may include determining that the hypertension in the patient is orthostatic based on the comparison. The method may include applying the renal denervation energy to the patient based on the hypertension in the patient being orthostatic and a treatment model so that the application of the renal denervation energy may be tailored to the patient.

The method may include predicting an effectiveness or a responsiveness of the application of the renal denervation energy to the patient. The prediction may be based on a treatment model and may be done prior to applying the renal denervation energy to the patient.

In another aspect, the subject matter is embodied in a therapeutic assembly for renal denervation. The therapeutic assembly includes an energy delivery element. The energy delivery element is configured to provide renal denervation energy to a nerve within a blood vessel of a patient. The therapeutic assembly includes a controller. The controller is coupled to the energy delivery element. The controller is configured to determine that the hypertension in the patient is orthostatic. The controller is configured to apply renal denervation energy to the patient using the energy delivery element.

In another aspect, the subject matter is embodied in a method for treatment of hypertension in a patient. The method includes measuring a supine blood pressure of the patient when the patient is in a supine position. The method includes measuring a standing blood pressure of the patient when the patient in a standing position. The method includes comparing the supine blood pressure to the standing blood pressure. The method includes determining that the hypertension in the patient is orthostatic based on the comparison. The method includes predicting an effectiveness or a responsiveness of renal denervation therapy to the patient. The method includes providing the predicted effectiveness or the predicted responsiveness to an operator.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views.

FIG. 13 is tabular presentation of statistical analysis of interactions between treatment and orthostatic hypertension under the first definition of orthostatic hypertension using the therapeutic assembly of FIG. 1 according to an aspect of the invention.

FIG. 14 is a table summarizing example blood pressure responses for patients that received RDN under the first definition of orthostatic hypertension using the therapeutic assembly of FIG. 1 according to an aspect of the invention.

FIG. 20 is tabular presentation of statistical analysis of interactions between treatment and orthostatic hypertension under the second definition of orthostatic hypertension using the therapeutic assembly of FIG. 1 according to an aspect of the invention.

FIG. 21 is a table summarizing example blood pressure responses for patients that received RDN under the second definition of orthostatic hypertension using the therapeutic assembly of FIG. 1 according to an aspect of the invention.

DETAILED DESCRIPTION

Disclosed herein are systems, devices, methods and/or apparatuses to detect or determine the effectiveness or the responsiveness of renal denervation therapy on hypertensive patients. In an analysis of renal denervation in patients with uncontrolled hypertension in the absence of antihypertensive medications it was revealed that renal denervation is more likely to be effective in patients with orthostatic hypertension than in patients without orthostatic hypertension, and so, the therapeutic assembly determines the type of hypertension to better understand the predicted effectiveness or responsiveness to the renal denervation therapy.

The therapeutic assembly determines whether hypertension within a patient is orthostatic and is able to predict the effectiveness or the responsiveness of the renal denervation therapy on the patient. The therapeutic assembly may use a treatment model to predict the effectiveness or the responsiveness of the renal denervation therapy on the patient, which allows an operator, such as a doctor, nurse or other healthcare professional to better assess the risks and likely outcomes of the renal denervation therapy to the specific patient. This minimizes the application or use of ineffective procedures and allows for the operator to anticipate any necessary follow-up treatments or procedures.

Other benefits and advantages include the capability to determine the most effective application of the renal denervation energy to treat a condition. The therapeutic assembly may use the analysis of the effectiveness or responsiveness of the patient to renal denervation therapy to determine an amount of renal denervation energy to deliver, a frequency of delivery for the renal denervation energy over a period of time and/or the number of times that the renal denervation energy should be applied. The therapeutic assembly may automatically control the delivery of the renal denervation energy based on the determined course of treatment and apply the renal denervation energy to the nerves within the wall of the blood vessel to attain the desired result, such as the mitigation of a symptom, a biological parameter, such as blood pressure, or a condition of a disease.

Figure 1:
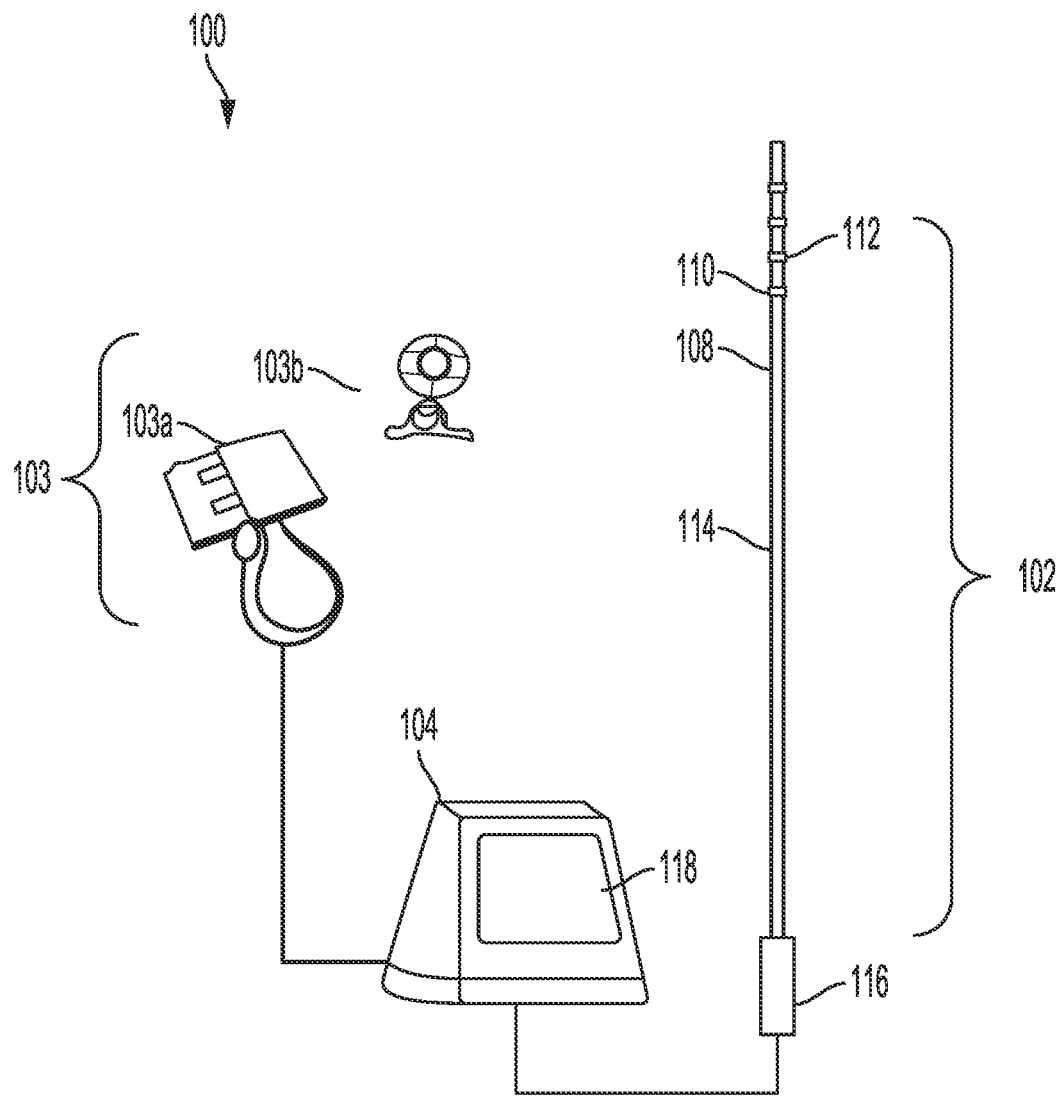
FIG. 1 shows an example conceptual illustration of the therapeutic assembly according to an aspect of the invention.

FIG. 1 shows the therapeutic assembly 100. The therapeutic assembly 100 performs renal denervation within the renal artery of a human patient. Renal denervation is a minimally invasive procedure to treat hypertension. The therapeutic assembly 100 may perform the renal denervation endovascularly, intravascularly or externally from the human patient. For example, the therapeutic assembly 100 may be a transducer positioned external to the human patient to deliver ultrasound energy into the body of the human patient. In another example, the therapeutic assembly 100 may be include a catheter or other device that is inserted into the human patient, such as via a small incision.

The therapeutic assembly 100 includes a renal denervation device 102 and/or a generator 104. The therapeutic assembly 100 may include or be coupled to one or more sensors 103, such as a sphygmomanometer, blood pressure gauge or blood pressure monitor 103a, which may be used to measure the blood pressure of the human patient. The one or more sensors 103 that measure the blood pressure of the human patient may measure the systolic blood pressure (SBP) and/or the diastolic blood pressure (DBP). The SBP and/or the DBP may be measured when the human patient is in the supine position and/or the standing position. The one or more sensors 103 may include a camera 103b or other position sensor. The position sensor may be a sensor that detects a position of the human patient, such as when the human patient is lying down, e.g., in a supine position, and/or standing up, e.g., in a standing position. The camera 103b may capture image data of the human patient, which a processor, such as the controller within the generator 104 may analyze to determine the position of the human patient. The one or more sensors 103 may be integrated within, coupled to or otherwise connected to the generator 104.

The renal denervation device 102 may include any device that delivers energy or stimulus to a target nerve within a wall of a blood vessel, such as the renal nerve of the renal artery. The device that delivers the energy or stimulus to the target nerve may be positioned external to the human patient, such as a transducer that emits ultrasound energy, or may be intravascularly positioned within the blood vessel to deliver the energy or stimulus, such as the renal denervation device 102. The energy or stimulus may include, for example, at least one of a radio frequency stimulus, a thermal stimulus, a cryogenic stimulus, a microwave stimulus, an ultrasonic or ultrasound stimulus or other form of energy or stimulus. Regardless of the type of energy delivered, the renal denervation device 102 does not fully occlude the blood vessel, and thus, blood may continue to flow through the blood vessel.

Figure 2A:
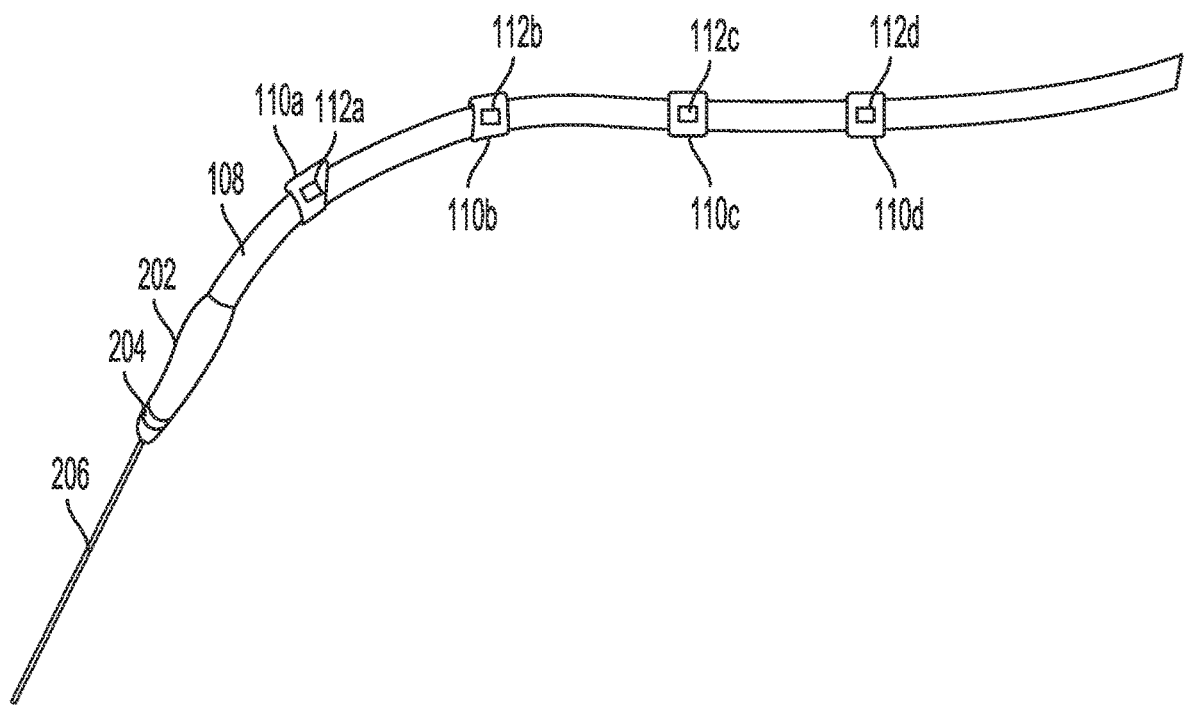
FIG. 2A shows an example renal denervation device of the therapeutic assembly of FIG. 1 in a low-profile delivery configuration according to an aspect of the invention.
Figure 2B:
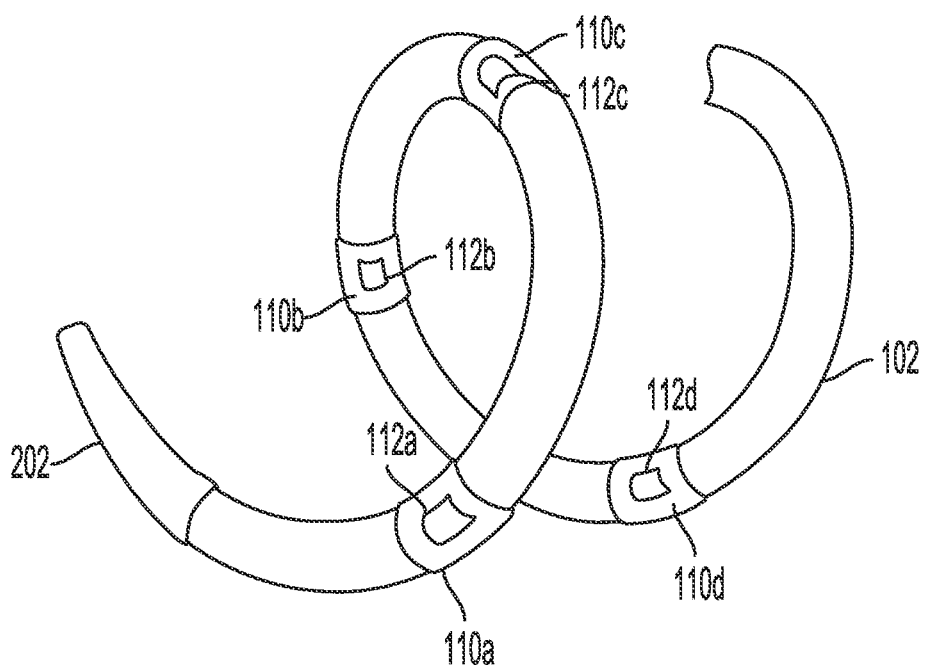
FIG. 2B shows an example renal denervation device of the therapeutic assembly of FIG. 1 in an expanded deployed configuration according to an aspect of the invention.
Figure 3:
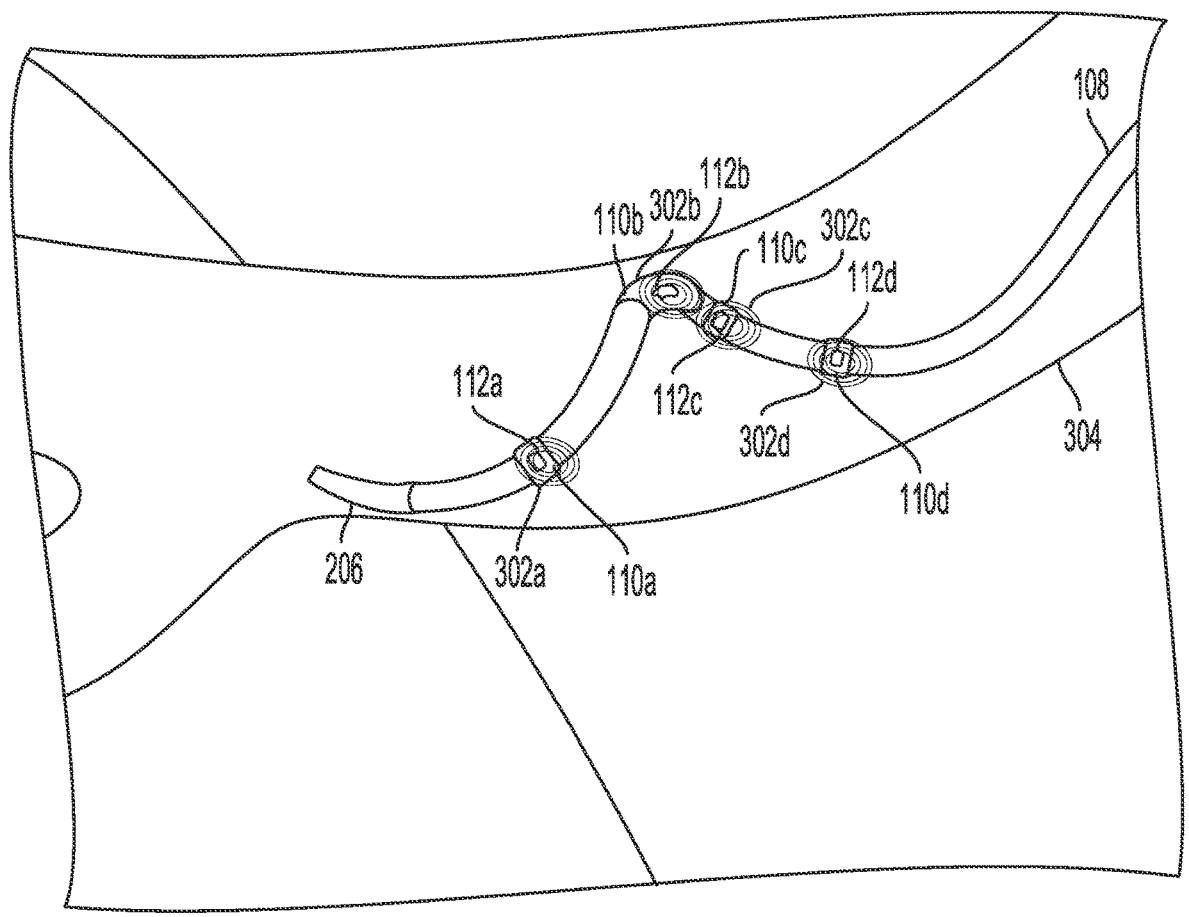
FIG. 3 shows an example renal denervation device of the therapeutic assembly of FIG. 1 in the expanded deployed configuration within a blood vessel according to an aspect of the invention.

The renal denervation device 102 may have a catheter 108 and/or one or more energy delivery elements 110, such as an electrode, and/or one or more sensors 112, such as a temperature sensor, blood flow sensor, impedance sensor or other sensor to interpolate characteristics of the heart rate, blood flow, blood pressure or other parameter. The renal denervation device 102 may have an elongated shaft 114 with a handle 116. The elongated shaft 114 with the handle 116 may be used to guide and/or advance a distal portion of the catheter 108 through the blood vessels of the patient, such as a human patient, to a target location of a blood vessel and remotely manipulate the distal portion of the catheter 108. The catheter 108 may be intravascularly delivered into the patient, e.g., a blood vessel of the patient, in a low-profile configuration, such as the substantially straight configuration shown in FIGS. 1 and 2A. The catheter 108 may be over a meter in length. Upon delivery to a target location within and along the blood vessel, the catheter 108 may be deployed into an expanded deployed configuration, such as a generally helical or spiral configuration or other suitable configuration, which the one or more energy delivery elements 110, such as one or more electrodes, may contact the blood vessel, as shown in FIG. 3 for example. In the expanded deployed state, the renal denervation device 102 may deliver energy at a treatment site and provide therapeutically-effective electrical and/or thermally induced denervation to a nerve within the wall of the blood vessel. FIGS. 2A-2B show the deployment of the renal denervation device 102. In particular, FIG. 2A shows the catheter 108 in the low-profile configuration, and FIG. 2B shows the catheter 108 in the expanded deployed configuration.

The catheter 108 may have a distal tip 202. The distal tip 202 points into the lumen of the blood vessel. The distal tip 202 may have a high density marker band 204. The high density marker band 204 allows a clinician to identify the distal tip 202 of the catheter 108 under fluoroscopy. The distal tip 202 may be approximately 4 cm-5 cm in length.

The catheter 108 may have a wire 206 within the lumen of the catheter 108. The distal tip 202 allows the wire 206 to extend out and away from the distal tip 202 when the catheter 108 is in the low-profile configuration and to be advanced through the blood vessels to the target location of the blood vessel. When the wire 206 is retracted within the distal tip 202 and into the catheter 108, the catheter 108 changes shape from the low-profile configuration, such as the substantially straight configuration, as shown in FIG. 2A for example, to the expanded deployed configuration, such as a generally helical or spiral configuration, as shown in FIG. 2B for example.

The renal denervation device 102 has one or more energy delivery elements 110. The one or more energy delivery elements 110 may include an electrode, such as a radiofrequency electrode, a radiofrequency probe, a thermal probe, a cryogenic probe, a microwave probe, an ultrasonic probe, an optical source or a chemical injector. The one or more energy delivery elements 110 may be positioned on the distal portion of the catheter 108. The one or more energy delivery elements 110 may include multiple energy delivery elements 110, such as the energy delivery elements 110a-d, as shown in FIGS. 2A, 2B and 3 for example. The energy delivery elements 110a-d may be arranged approximately 90 degrees apart relative to a longitudinal axis that runs through the center of the catheter 108 when in the spiral configuration. The energy delivery elements 110 may be spaced any suitable distance from each other, and the spacing may vary based on the application of the therapeutic assembly 100 and its intended use.

When there are multiple energy delivery elements 110, each energy delivery element 110 may deliver power independently, either simultaneously, selectively, and/or sequentially, to a treatment site. The multiple energy delivery elements 110 may deliver power among any desired combination of the one or more energy delivery elements 110. The multiple energy delivery elements 110 may include any number of energy delivery elements 110.

The one or more energy delivery elements 110 may be introduced into and advanced along a blood vessel 304, such as the renal artery and may be positioned to contact the blood vessel 304 in the expanded deployed configuration at different intervals and/or locations along the wall of the blood vessel 304. For example, a first energy delivery element 110a may contact the wall of the blood vessel 304 at a first location 302a, a second energy delivery element 110b may contact the wall of the blood vessel 304 at a second location 302b, a third energy delivery element 110c may contact the wall of the blood vessel 304 at a third location 302c and a fourth energy delivery element 110d may contact the wall of the blood vessel 304 at a fourth location 302d. The renal denervation device 102 may deliver energy through the one or more energy delivery elements 110 at the treatment site and provide therapeutically-effective electrically- and/or thermally-induced denervation.

The renal denervation device 102 may include one or more sensors 112. The one or more sensors 112 may be a sensor that measures a parameter, such as temperature, impedance, blood pressure, optical, blood flow, or amount of chemical. The one or more sensors 112 may be proximate to or within the energy delivery element 110. The measured parameter may be used to interpolate another parameter. For example, measured temperature may be used to interpolate the heart rate of the patient.

Each of the one or more sensors 112 may be coupled to, integrated with or in a close proximity to a corresponding one of the one or more energy delivery elements 110. This allows each of the one or more sensors 112 to measure the parameter local to the energy delivery element 110 so that the parameter reflects to the effects of the energy delivery element 110 on the location tissue. For example, the first sensor 112a may be integrated with the first energy delivery element 110a, the second sensor 112b may be integrated with second energy delivery element 110b, the third sensor 112c may be integrated with the third energy delivery element 110c and the fourth sensor 112d may be integrated with the fourth energy delivery element 110d, as shown in FIG. 2B for example.

For example, the energy delivery element 110 may be an electrode, which has two wires. One wire may be made from copper and the other may be made from a copper-nickel allow. The wires may both transmit the signal from the sensor 112 and also convey the energy to the energy delivery element. The signal may be a temperature signal that indicates the temperature of the blood vessel, a pressure signal that indicates the blood flow or pressure near the location targeted by the electrode.

The therapeutic assembly includes a generator 104. The generator 104 may be a radio frequency generator or other generator that delivers a denervation stimulus or energy through the one or more energy delivery elements 110 to the wall of the blood vessel at the treatment location. The denervation stimulus may include a non-electric stimulus, for example, a chemical agent, optical stimulus, a thermal stimulus, a cooling stimulus, a microwave stimulus or other form of stimuli. The generator 104 may have a cable, an electrical lead and/or wire that is electrically conductive and runs through the catheter 108 within a lumen and is electrically coupled with the one or more energy delivery elements 110. In some implementations, the generator 104 may have separate leads and/or wires that electrically couple with a corresponding energy delivery element 110 of the one or more energy delivery elements 110 so that each energy delivery element 110 may operate independently of the others. For example, the generator 104 may have multiple separate channels, such as four RF channels to deliver RF energy independently to the energy delivery elements 110a-d and control and monitor each energy delivery element 110a-d independently. The generator 104 may generate energy that ultimately is transmitted through the electrical lead to the one or more energy delivery elements 110.

Figure 4:
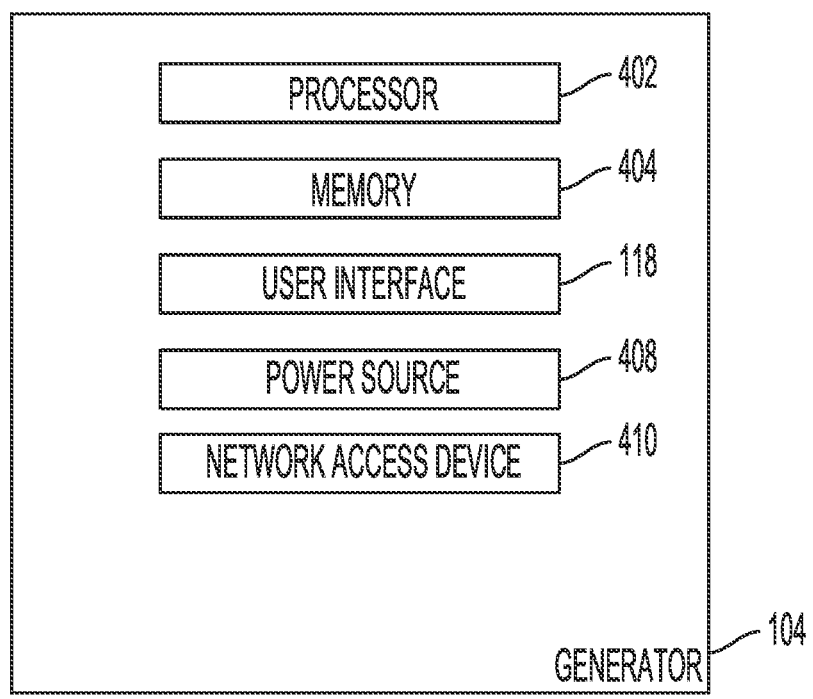
FIG. 4 is a block diagram of an example generator of the therapeutic assembly of FIG. 1 according to an aspect of the invention.

The generator 104 may have one or more processors 402, a memory 404, a user interface 118, a network access device 410 and/or a power source 408, as shown in FIG. 4 for example. The one or more processors 402 may be electrically coupled to the memory 404, the user interface 118 and/or the power source 408. The one or more processors 402 may include one or more controllers that measure the blood pressure of the human patient, formulate or predict the effectiveness or responsiveness of renal denervation therapy on the human patient and/or formulate and administer a course of treatment for the delivery of the renal denervation energy.

The one or more processors 402 may control a state of each of the one or more energy delivery elements 110 and the amount of energy delivered to each of the one or more energy delivery elements 110 by the power source 408 to manage the course and administration of treatment at the treatment site. The one or more processors may be coupled to the memory 404 and execute instructions that are stored in the memory 404.

The generator 104 may have a memory 404. The memory may be coupled to the one or more processors 402 and store instructions that the one or more processors 402 executes. The memory 404 may include one or more of a Random Access Memory (RAM), Read Only Memory (ROM) or other volatile or non-volatile memory. The memory 404 may be a non-transitory memory or a data storage device, such as a hard disk drive, a solid-state disk drive, a hybrid disk drive, or other appropriate data storage, and may further store machine-readable instructions, which may be loaded and executed by the one or more processors 402. The memory 404 may store one or more thresholds for the determination of whether the hypertension of the human patient is orthostatic or not, which may affect the predicted effectiveness or responsiveness of renal denervation therapy and/or the course of treatment for the delivery of the renal denervation energy to the human patient.

The generator 104 may have a power source 408, such as a RF generator or other electrical source. The power source 408 provides a selected form and magnitude of energy for delivery to the treatment site via the renal denervation device 102. The generator 104 may have a user interface 118. The generator 104 may receive input, such as the selected form and the magnitude of energy to be delivered to each of the one or more energy delivery elements 110, via the user interface 118. The user interface 118 may receive other user input including the blood pressure of the human patient and/or the position of the human patient, such as when the human patient is in the supine position or the standing position.

The user interface 118 may include an input/output device that receives user input from a user interface element, a button, a dial, a microphone, a keyboard, or a touch screen. The user interface 118 may provide an output to an output device, such as a display, a speaker, an audio and/or visual indicator, or a refreshable braille display. The output device may display an alert or notification or other information to the clinician and/or to confirm status and/or commands from the clinician. The output device may be an audio output device that outputs an audio indicator that indicates the notification or information to be provided to the clinician.

In some implementations, the camera 103b or other position sensor may be included within the generator 104. The camera 103b or other position sensor may be used to capture data, such as image data, to determine the position of the human patient, such as whether the human patient is in the supine position or the standing position.

The network access device 410 may include a communication port or channel, such as one or more of a Dedicated Short-Range Communication (DSRC) unit, a Wi-Fi unit, a Bluetooth® unit, a radio frequency identification (RFID) tag or reader, or a cellular network unit for accessing a cellular network (such as 3G, 4G or 5G). The network access device 410 may transmit data to and receive data from an external database or remote server.

Figure 5:
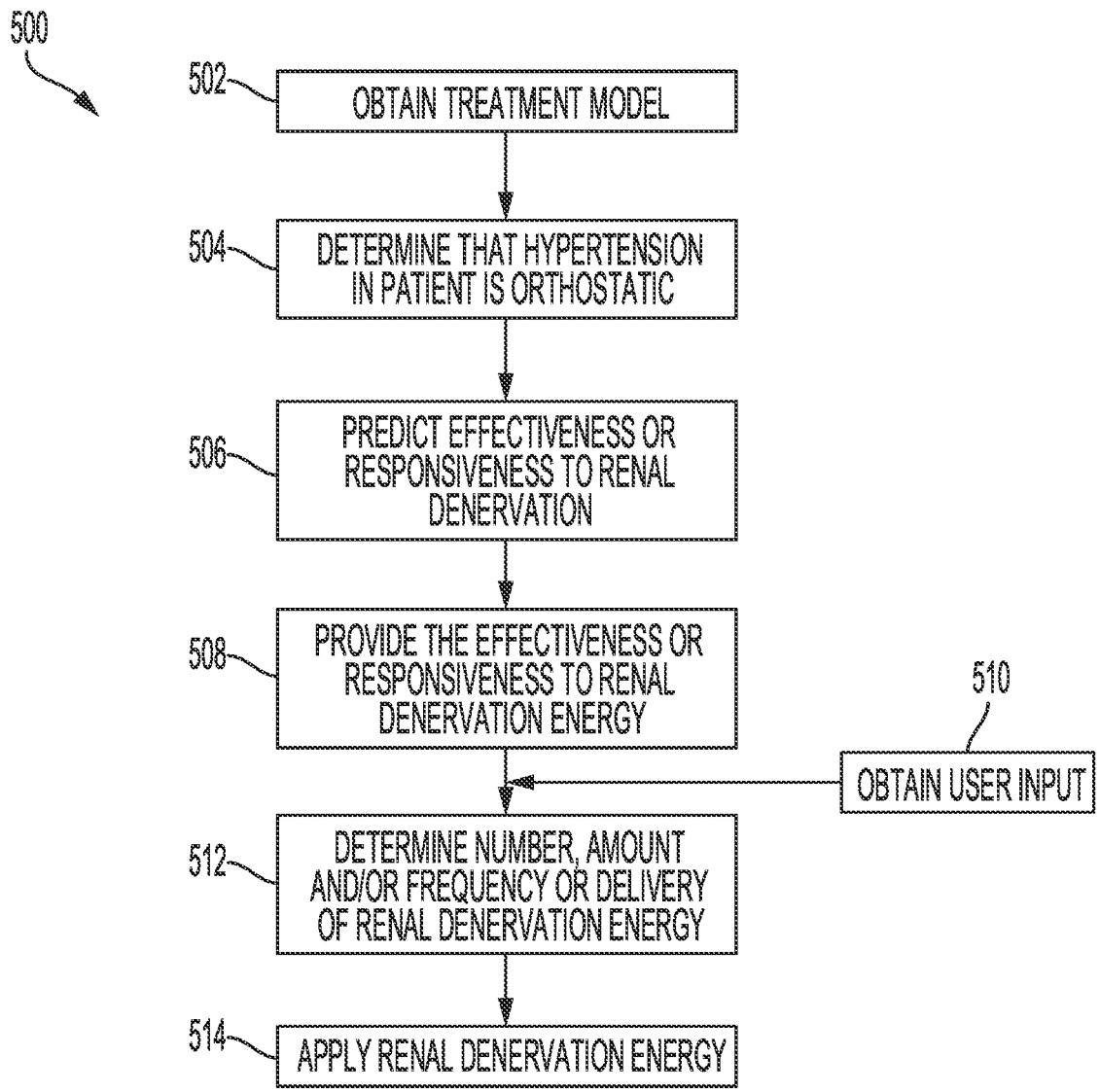
FIG. 5 is a flow diagram of an example process for controlling the energy delivered to the one or more energy delivery elements of the therapeutic assembly of FIG. 1 according to an aspect of the invention.

FIG. 5 is a flow diagram of a process 500 for controlling the energy delivered to the one or more energy delivery elements 110. One or more computers or one or more data processing apparatuses, for example, the processor 402 of the generator 104 of the therapeutic assembly 100 of FIG. 1, appropriately programmed, may implement the process 500.

The therapeutic assembly 100 includes a generator 104, which controls the delivery of energy to the one or more energy delivery elements 110 of the renal denervation device 102. The therapeutic assembly 100 may receive or obtain a treatment model (502). The treatment model may be based on an accumulation of population patient data that corresponds to various characteristics or parameters of a human patient, various treatments, various disease conditions and/or the corresponding and/or resulting effectiveness and/or responsiveness of the delivered energy for each of the disease conditions when following the corresponding treatment. The treatment model may be generated from population patient data that is generated in real-time along with experimental data from clinical trials, such as the experimental data presented in FIGS. 8-21, to identify the effectiveness and/or responsiveness of the renal denervation on patients with hypertension that is or is not orthostatic.

The characteristics or parameters of the human patient may include demographic data, age, sex, body mass index (BMI), blood pressure values, cholesterol level, activity level, sleeping habits and/or other characteristics or parameters of the human patient. The various treatments may be associated with the amount of energy delivered, the frequency of the amount of energy delivered over a period of time, the length of the period of time of the continued delivery of the energy and/or the location and/or treatment site where the energy is delivered. The disease conditions may include various diseases, such as a heart condition or disease, a gastrointestinal condition or disease, an immunological or respiratory condition or disease and/or other condition or disease. The effectiveness and/or responsiveness of the delivered energy for each of the disease conditions may include a likelihood and/or an amount of improvement of a parameter associated or related to the disease or condition, such as a decrease in blood pressure of approximately 10%-15% or a decrease in the likelihood of a heart condition of approximately 10%-15%. The treatment model relates or maps each of these factors with the other factors so that the treatment model may be used to anticipate or predict that a human patient with a specific set of characteristics or parameters, such as particular body weight, height, level of activity or other characteristics or parameters, when given a particular course of treatment, such as an ablation once a month for a couple months, will likely result in a given effectiveness and/or responsiveness to the disease or condition, such as a decrease in the likelihood of a heart condition.

The therapeutic assembly 100 may obtain the treatment model via user input through the user interface 118. In some implementations, the therapeutic assembly may obtain the treatment model from an external database or a remote server via the network access device 410.

Figure 6:
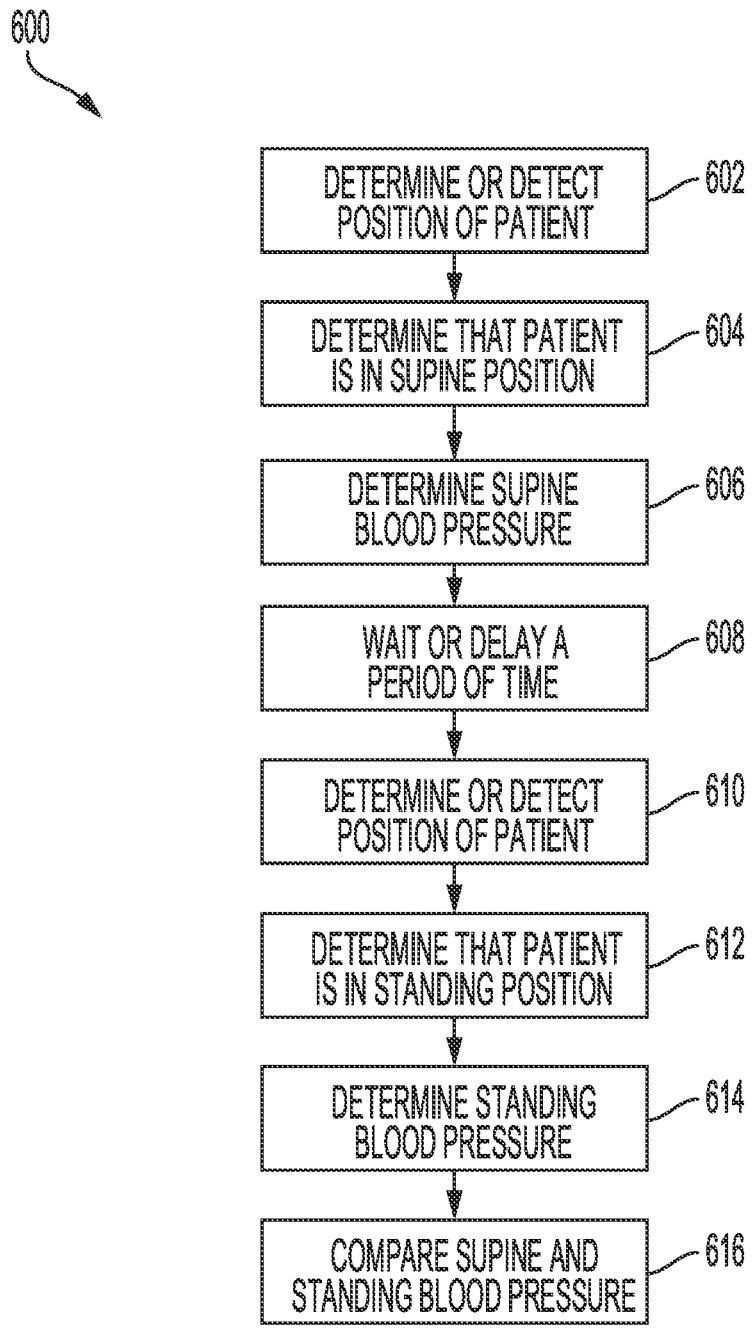
FIG. 6 is a flow diagram of an example process for determining the blood pressure of the human patient using the therapeutic assembly of FIG. 1 according to an aspect of the invention.
Figure 7:
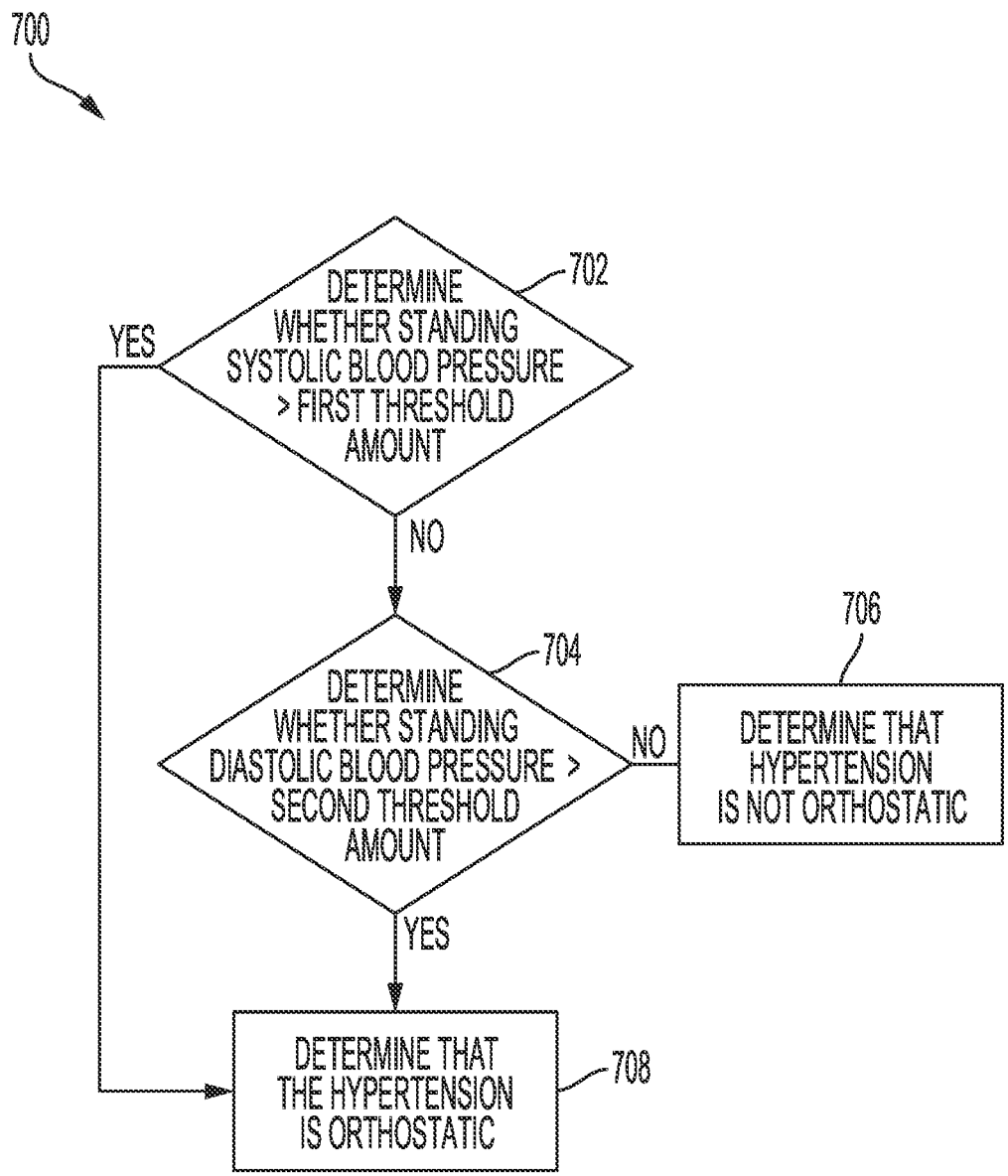
FIG. 7 is a flow diagram of an example process for comparing the blood pressure of the human patient when in the standing position and in the supine position to determine whether the hypertension is orthostatic using the therapeutic assembly of FIG. 1 according to an aspect of the invention.

The therapeutic assembly 100 may determine that the hypertension in a human patient is orthostatic (504). The therapeutic assembly 100 may collect or obtain sensor data and/or user input to determine whether the hypertension in the patient is orthostatic. If the hypertension is orthostatic, the delivery of the energy may be more effective in treating the disease or condition of the patient. And if the hypertension is not orthostatic, the delivery of the energy may be less effective than when the hypertension is orthostatic. FIGS. 6-7 further describe the process for determining whether the hypertension in the human patient is or is not orthostatic.

The therapeutic assembly 100 may predict the effectiveness or responsiveness to application of the renal denervation energy (506). The effectiveness or the responsiveness may be based on whether the hypertension is orthostatic or not. A patient with hypertension that is orthostatic may be more responsive to the application of the renal denervation energy, and so, the therapeutic assembly 100 may account for whether the hypertension is orthostatic or not when determining the effectiveness or the responsiveness.

The therapeutic assembly 100 may use the treatment model to predict the effectiveness or responsiveness to the application of the renal denervation energy prior to applying the renal denervation energy to a treatment site. The effectiveness or responsiveness may be a measure, a probability and/or a likelihood that the renal denervation energy may improve a disease or condition.

The improvement of the disease or condition may be determined by an amount of change or improvement in a parameter associated with the disease or condition, such as a decrease in blood pressure, a decrease in cholesterol and/or other parameter when relating to a heart disease, for example. The improvement of the disease or condition may be determined by the elimination or reduction in a symptom caused by the disease or condition, or the elimination or reduction in a measurable quantity of the disease or condition within the human patient, as determined by a doctor, nurse or other health care professional who provides the qualitative or quantitative success, partial success or failure in the elimination or reduction in the symptom, condition and/or disease. The probability and/or the likelihood may be quantified as a percentage of success or a percentage of failure that represents the overall improvement of the condition or disease relative to non-treatment or non-use of renal denervation energy to innervate the treatment site. As shown in FIGS. 8-21 below, the improvement in the symptom, condition and/or disease is greater in patients with hypertension that is orthostatic.

The therapeutic assembly 100 may provide the effectiveness or the responsiveness to the delivery of the renal denervation energy to a clinician, such as a doctor, nurse or other health care professional (508). The therapeutic assembly 100 may display the effectiveness or the responsiveness on the user interface 118, such as on the display, to present to the clinician the effectiveness or the responsiveness to the delivery of the renal denervation energy. When providing the effectiveness or the responsiveness, the therapeutic assembly 100 may indicate the likelihood or probability of success, partial success, and/or failure and/or the predicted resulting state of the disease or condition after delivery of the renal denervation energy. This allows the operator to analyze and review the anticipated outcome of the application of the renal denervation energy before the human patient undergoes renal denervation therapy.

In some implementations, the therapeutic assembly 100 may simultaneously request confirmation that the clinician would like the therapeutic assembly 100 to proceed with applying renal denervation energy to the treatment site when providing the effectiveness or responsiveness to the renal denervation energy. This allows the clinician to weigh the costs and benefits of the application of the renal denervation energy and inform the human patient of the predicted consequences of the application of the renal denervation energy.

The therapeutic assembly 100 may obtain user input (510). The therapeutic assembly 100 may obtain user input that indicates or confirms that the clinician desires to apply the renal denervation energy to the treatment site. The user input may be received via the user interface 118. This allows the clinician to confirm that the therapeutic assembly 100 should proceed with renal denervation therapy.

The therapeutic assembly 100 may determine the course of treatment including the number of times, amount and/or frequency of delivery of the renal denervation energy to the treatment site (512). The course of treatment may also indicate a treatment site or location of which the renal denervation energy should be applied or delivered. The treatment strategy, such as the aggressiveness of the course of treatment, may be affected by whether the hypertension is determined to be orthostatic or not orthostatic.

The number of times may indicate the number of different times that the human patient must receive the course of treatment to achieve the predicted effectiveness and/or responsiveness to the renal denervation energy for the condition or disease of the human patient. The amount may indicate the magnitude of the amount of renal denervation energy delivered for each time that the renal denervation energy is applied or is delivered to the human patient. The frequency may indicate the number of times within each period of time and the number of periods of time of which the renal denervation energy should be applied or delivered to the human patient for the course of treatment, such as once a week for a period of 3 months.

The therapeutic assembly 100 may determine the course of treatment using the treatment model and the specific characteristics, features and parameters of the human patient. The therapeutic assembly 100 may compare the specific characteristics, features and parameters of the human patient and identify similar patients within the treatment model with those same or corresponding specific characteristics, features and parameters to identify the course of treatment that provides the greatest likelihood or probability of success for the condition or disease. The treatment model allows the therapeutic assembly 100 to tailor the course of treatment to the specific human patient, which increases the chance of success for the individual.

Once the course of treatment is generated, the therapeutic assembly 100 delivers or applies the renal denervation energy to the treatment site (514). The therapeutic assembly 100 may use the generator 104 to generate energy or stimuli to deliver through the one or more energy delivery elements 110 at the treatment site. In some implementations, the therapeutic assembly 100 may identify that the one or more energy delivery elements 110 are positioned at the treatment site prior to the delivery of the energy or stimuli. The therapeutic assembly 100 may deliver or apply the renal denervation energy to the treatment site only when the user has confirmed that the application of the renal denervation energy is to proceed or may delivery or apply the renal denervation energy automatically.

FIG. 6 is a flow diagram of a process 600 for determining the blood pressure of the human patient. One or more computers or one or more data processing apparatuses, for example, the processor 402 of the generator 104 of the therapeutic assembly 100 of FIG. 1, appropriately programmed, may implement the process 600.

The therapeutic assembly 100 may determine or detect a position of the human patient (602). The therapeutic assembly 100 may use one or more sensors 103, such as the camera 103b, to determine or detect the position of the human patient. For example, the camera 103b may capture image data of the human patient and analyze the human patient to determine the position of the human patient, such as the orientation of the human patient. The therapeutic assembly 100 may use the orientation of the human patient to determine whether the human patient is in a standing or supine position. In another example, the therapeutic assembly 100 may have one or more sensors 103 coupled to the body of the human patient, which assists the therapeutic assembly 100 in determining the position, such as the orientation, of the human patient to determine whether the human patient is in a standing or supine position.

The therapeutic assembly 100 determines that the human patient is in the supine position (604). The therapeutic assembly 100 may determine that the human patient is in the supine position based on the orientation of the human patient relative to a planar surface, such as the floor. The therapeutic assembly 100 may analyze the image data and recognize the human patient and the planar surface, such as the floor, by comparing the outline or skeleton of the human patient and the planar surface to a library of objects to identify the human patient and the planar surface. Once recognized, the position including the orientation of the human patient may be compared to the planar surface to determine whether the human patient is parallel to the planar surface, and when the human patient is parallel to the planar surface, the therapeutic assembly 100 may determine that the human patient is in the supine or lying position.

In some implementations, the therapeutic assembly 100 may receive user input, such as from the clinician, to determine that the human patient is in the supine position. The therapeutic assembly 100 may receive the user input via the user interface 118. The user input may indicate the position including the orientation of the human patient, such as whether the human patient is in the supine, standing or other position. The therapeutic assembly 100 may determine that the human patient is in the supine position when the user input indicates that the human patient is in the supine position.

Once the human patient is determined to be in the supine position, the therapeutic assembly 100 may measure, obtain or otherwise determine the supine blood pressure of the human patient (606). The supine blood pressure is the blood pressure of the human patient while the human patient is in the supine position. The supine blood pressure includes the systolic blood pressure (SBP) and the diastolic blood pressure (DBP) when the human patient is in the supine or lying position. The therapeutic assembly 100 may use one or more sensors 103, such as the blood pressure monitor 103a, to obtain the supine blood pressure. The blood pressure monitor may be coupled or connected to the human patient while the human patient is in the supine position to measure the supine blood pressure of the human patient while the human patient is in the supine position. In some implementations, the therapeutic assembly 100 may receive or obtain the supine blood pressure via user input on the user interface 118 that indicates the supine blood pressure. For example, the clinician may use the blood pressure monitor 103a to measure the supine blood pressure and input the supine blood pressure into therapeutic assembly 100 via the user interface 118.

After the supine blood pressure is measured and determined, the therapeutic assembly 100 may wait or delay a period of time before the therapeutic assembly 100 attempts to measure the standing blood pressure (608). The period of time may be approximately 5-10 minutes to allow the physiological parameters of human patient to transition from the supine position to a standing position. The period of time may be user-configured, user-inputted or pre-determined. In some implementations, the therapeutic assembly 100 may request a user confirmation before proceeding with determining the standing blood pressure. The therapeutic assembly 100 may proceed with determining the standing blood pressure after receiving the user confirmation.

After the period of time, the therapeutic assembly 100 repeats determining or detecting the position of the human patient, as described above (610). Then, the therapeutic assembly 100 determines that the human patient is in the standing position (612). The therapeutic assembly 100 may determine that the human patient is in the standing position based on the orientation of the human patient relative to a planar surface, such as the floor. Similar to detecting the supine position, the therapeutic assembly 100 may analyze the image data and recognize the human patient and the planar surface, such as the floor, by comparing the outline or skeleton of the human patient and the planar surface to a library of objects to identify the human patient and the planar surface. However, once recognized, the position including the orientation of the human patient may be compared to the planar surface to determine whether the human patient is perpendicular to the planar surface, and when the human patient is perpendicular to the planar surface, the therapeutic assembly 100 may determine that the human patient is in the standing position.

In some implementations, the therapeutic assembly 100 may receive user input, such as from the clinician, to determine that the human patient is in the standing position. The therapeutic assembly 100 may receive the user input via the user interface 118. The user input may indicate the position including the orientation of the human patient, such as whether the human patient is in the supine, standing or other position. The therapeutic assembly 100 may determine that the human patient is in the standing position when the user input indicates that the human patient is in the standing position.

Once the human patient is determined to be in the standing position, the therapeutic assembly 100 may measure, obtain or otherwise determine the standing blood pressure of the human patient (614). The standing blood pressure is the blood pressure of the human patient while the human patient is in the standing position. The standing blood pressure includes the systolic blood pressure (SBP) and the diastolic blood pressure (DBP) when the human patient is in the standing position. The therapeutic assembly 100 may use one or more sensors 103, such as the blood pressure monitor 103a, to obtain the standing blood pressure. The blood pressure monitor may be coupled or connected to the human patient while the human patient is in the standing position to measure the standing blood pressure of the human patient while the human patient is in the standing position. In some implementations, the therapeutic assembly 100 may receive or obtain the standing blood pressure via user input on the user interface 118 that indicates the standing blood pressure. For example, the clinician may use the blood pressure monitor 103a to measure the standing blood pressure and input the standing blood pressure into therapeutic assembly 100 via the user interface 118.

After the standing blood pressure and the supine blood pressure are measured, obtained or otherwise determined, the therapeutic assembly 100 may compare the supine and the standing blood pressure (616). The therapeutic assembly 100 may compare the supine systolic blood pressure to the standing systolic blood pressure and/or the supine diastolic blood pressure to the standing diastolic blood pressure. The therapeutic assembly 100 may use the comparison to determine whether the hypertension in the patient is orthostatic. FIG. 7 further describes the comparison of the blood pressures to determine whether the hypertension in the patient is orthostatic. In some implementations, a clinician performs the comparison of the standing blood pressure and the supine blood pressure and determines whether the hypertension in the patient is orthostatic and/or whether the patient is a good candidate for renal denervation after measuring the supine and standing blood pressures.

FIG. 7 is a flow diagram of a process 700 for comparing the blood pressure of the human patient when in the standing position and in the supine position to determine whether the hypertension is orthostatic. One or more computers or one or more data processing apparatuses, for example, the processor 402 of the generator 104 of the therapeutic assembly 100 of FIG. 1, appropriately programmed, may implement the process 700. When determining whether the hypertension is orthostatic, the orthostatic or postural hypertension may be defined in two alternatives. The first definition of orthostatic hypertension requires a patient's baseline standing systolic blood pressure (SBP) to be greater than baseline supine SBP by 20 mmHG or more, or a patient's baseline standing diastolic blood pressure (DBP) to be greater than a baseline supine DBP by 20 mmHg or more. The second definition of orthostatic hypertension requires a patient's baseline standing systolic blood pressure (DBP) to be greater than a baseline supine SBP by 10 MMHG or more, or a patient's baseline standing diastolic blood pressure (DBP) to be greater than a baseline supine DBP by 10 mmHG or more. The therapeutic assembly may implement the two definitions 100, as described below, to determine whether a patient has orthostatic hypertension.

When the therapeutic assembly 100 compares the standing and supine blood pressures, the therapeutic assembly 100 may compare the diastolic blood pressures and/or the systolic blood pressures of the human patient while standing and while lying down to determine whether the hypertension is orthostatic. The therapeutic assembly 100 determines whether the standing systolic blood pressure (SBP) is greater than a first threshold amount (702). The first threshold amount may be an amount that is at least 10 mmHG greater than the supine SBP, as defined by the second definition, or an amount that is at least 20 mmHG greater than the supine SBP, as defined by the first definition.

When the standing SBP is greater than the first threshold amount, the therapeutic assembly 100 may determine that the hypertension is orthostatic (708). The therapeutic assembly 100 may determine that the hypertension is orthostatic when the amount is at least 10 mmHG greater than the supine SBP, as defined by the second definition, or when the amount is at least 20 mmHG greater than the supine SBP, as defined by the first definition.

Otherwise, when the standing SBP is less than or equal to the first threshold amount, the therapeutic assembly 100 determines whether the standing diastolic blood pressure (DBP) is greater than a second threshold amount (704). The second threshold amount may be an amount that is at least 10 mmHG greater than the supine DBP, as defined in the second definition, or an amount that is at least 20 mmHG greater than the supine DBP, as defined by the first definition.

When the standing DBP is greater than the second threshold amount, the therapeutic assembly 100 determines that the hypertension is orthostatic (708). The therapeutic assembly 100 may determine that the hypertension is orthostatic when the amount is at least 10 mmHG greater than the supine DBP, as defined by the second definition, or when the amount is at least 20 mmHG greater than the supine DBP, as defined by the first definition.

Otherwise, the therapeutic assembly 100 determines that the hypertension is not orthostatic when the conditions are not met, as defined by the first definition or the second definition that is used to perform the determination (706). The determination of whether the hypertension is or is not orthostatic affects the effectiveness and/or the responsiveness of the application of renal denervation energy to treat the disease or condition. The definition that is to be satisfied to determine whether hypertension is orthostatic or not may be selected via user input to the user interface 118 and/or may be pre-configured or user-configured.

FIGS. 8-21 show the experimental analysis of a clinical trial studying renal denervation in patients with hypertension. The analysis looked for interactions between treatment, either RDN or control, and orthostatic hypertension for various use cases of blood pressure measures. The interaction shows the change in blood pressure in patients with orthostatic hypertension and in patients without orthostatic hypertension. The various use cases measured the systolic blood pressure at 3 months for the following time periods using the first and second definitions: 1) over 24 hours, 2) during the daytime (9 a.m. to 9 p.m. average), 3) during nighttime (1 a.m. to 6 p.m. average), 4) during the morning (7 a.m. to 9 a.m. average) and during peak morning (i.e. highest 1-hour moving average of at least 3 consecutive SBPs between 6 a.m. and 10 a.m.). Then, the analysis compared the response rates between RDN subjects with and without orthostatic hypertension for the same time periods.

Figure 8:
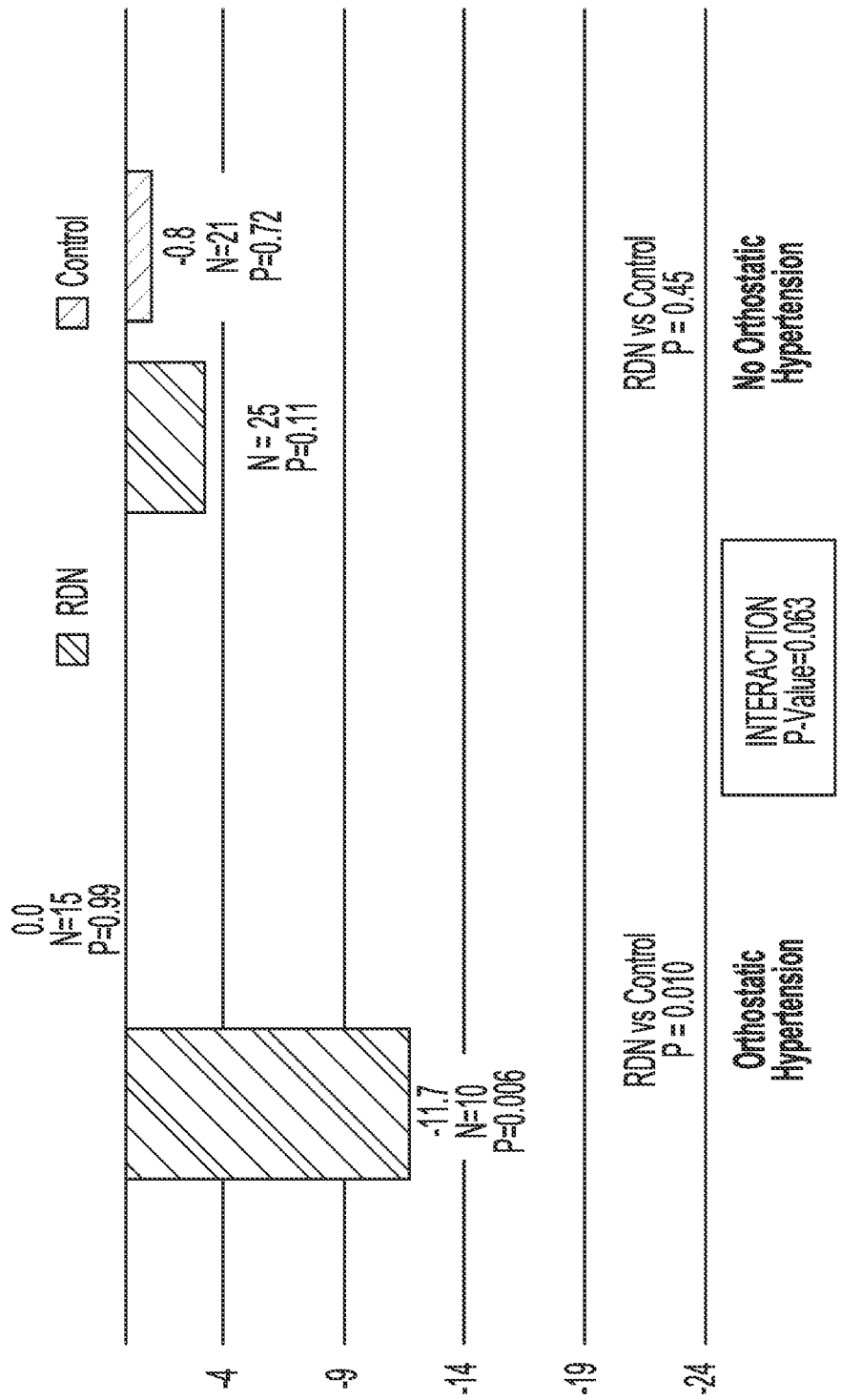
FIG. 8 is a bar chart that shows an example of blood pressure response to renal denervation to off-med patients at 3 months over 24 hours under a first definition of orthostatic hypertension using the therapeutic assembly of FIG. 1 according to an aspect of the invention.

FIG. 8 is a bar chart that shows the blood pressure response to renal denervation to off-med patients at 3 months over 24 hours under a first definition of orthostatic hypertension. The bar chart shows that among the number, N, subjects that the subjects that had orthostatic hypertension showed a greater change, i.e., decrease in SBP when RDN is performed in comparison to a control group, over the 24 hour period than the subjects that did not have orthostatic hypertension when RDN was performed. Thus, RDN was more effective in decreasing the SBP over the 24 hour period in patients with orthostatic hypertension.

Figure 9:
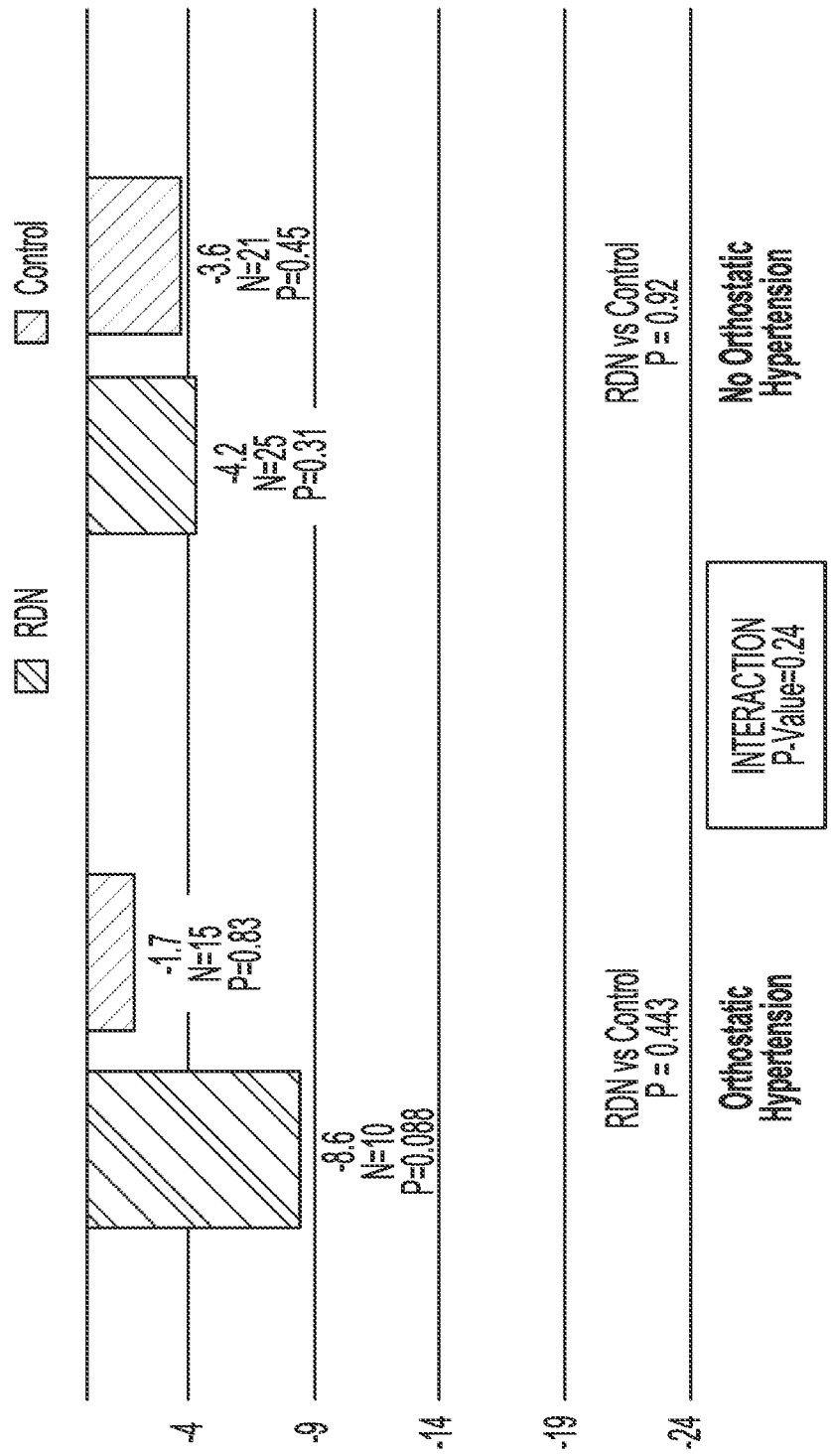
FIG. 9 is a bar chart that shows an example of blood pressure response to renal denervation to off-med patients at 3 months in the morning under a first definition of orthostatic hypertension using the therapeutic assembly of FIG. 1 according to an aspect of the invention.

FIG. 9 is a bar chart that shows the blood pressure response to renal denervation to off-med patients at 3 months in the morning under a first definition of orthostatic hypertension. Here, the subjects that had orthostatic hypertension showed a greater change, i.e., decrease in SBP when RDN is performed in comparison to a control group, over the morning period than the subjects that did not have orthostatic hypertension when RDN was performed. Similarly, the bar chart shows that RDN was more effective in decreasing the SBP over the morning period in patients with orthostatic hypertension.

Figure 10:
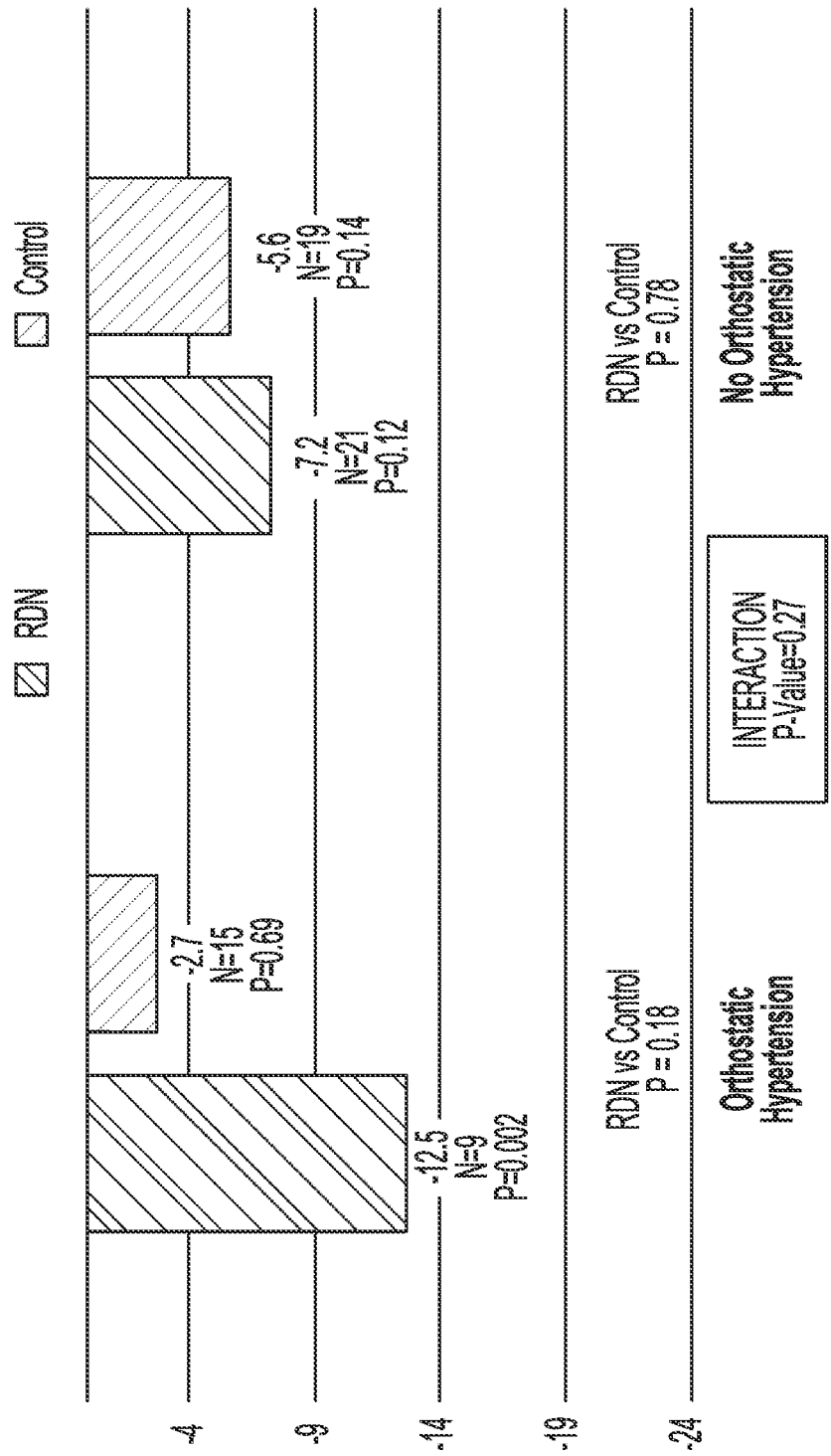
FIG. 10 is a bar chart that shows an example of blood pressure response to renal denervation to off-med patients at 3 months in the peak morning under a first definition of orthostatic hypertension using the therapeutic assembly of FIG. 1 according to an aspect of the invention.
Figure 11:
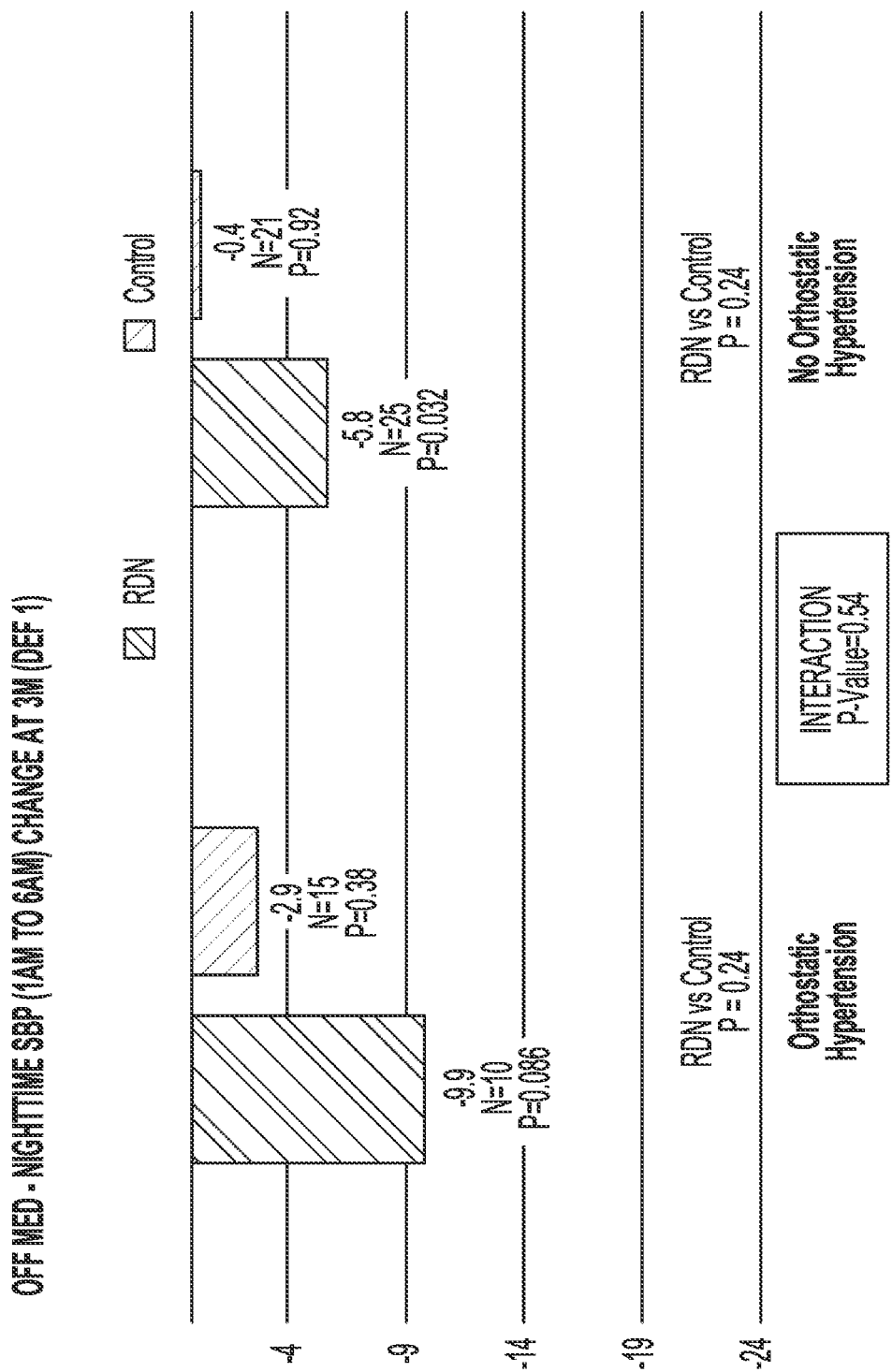
FIG. 11 is a bar chart that shows an example of blood pressure response to renal denervation to off-med patients at 3 months in the nighttime under a first definition of orthostatic hypertension using the therapeutic assembly of FIG. 1 according to an aspect of the invention.
Figure 12:
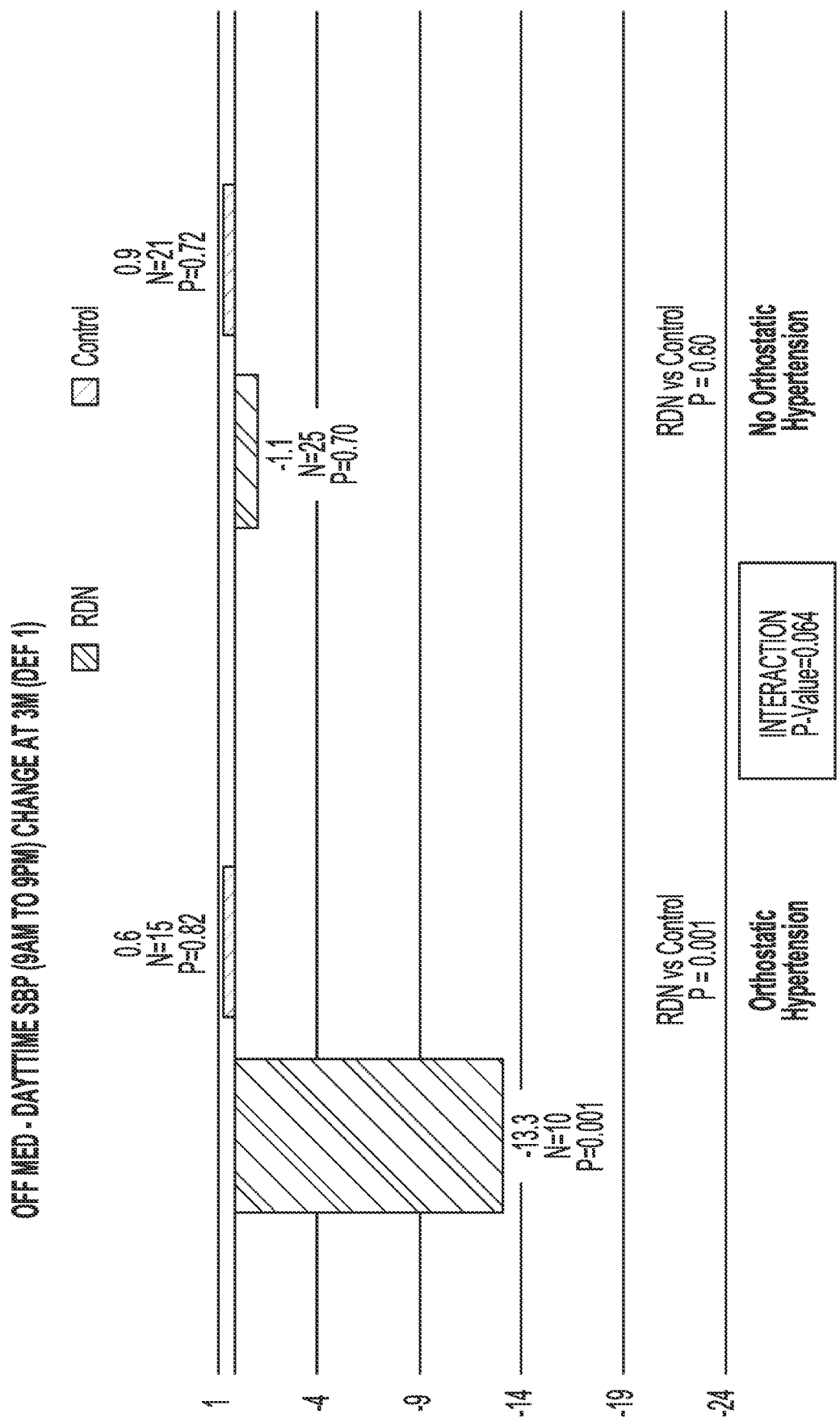
FIG. 12 is a bar chart that shows an example of blood pressure response to renal denervation to off-med patients in the daytime under a first definition of orthostatic hypertension using the therapeutic assembly of FIG. 1 according to an aspect of the invention.

FIGS. 10-12 show similar results showing the effectiveness of RDN in in patients with orthostatic hypertension. FIG. 10 shows the blood pressure response to renal denervation to off-med patients at 3 months in the peak morning under a first definition, and FIG. 11 shows response rates to renal denervation to off-med patients at 3 months in the nighttime under a first definition. Also, FIG. 12 shows the blood pressure response to renal denervation in off-med patients in the daytime under a first definition. In FIGS. 10-12, RDN is demonstrated to be more effective in patients with orthostatic hypertension than in patients with no orthostatic hypertension.

FIG. 13 is a tabular presentation of that summarizes the statistical analysis of the interactions between treatment of orthostatic hypertension patients and non-orthostatic hypertension patients under the first definition of orthostatic hypertension. The p-value is reported to identify the probability of obtaining results as extreme as the observed results of a statistical hypothesis test. A smaller p-value means that there is strong evidence in favor of the existence of a statistical significance in the RDN being more effective in orthostatic hypertension patients. A larger p-value means that there is weak or no evidence in favor of the existence of a statistical significance in the RDN being more effective in orthostatic hypertension patients. Generally, a threshold of 0.05 is used to determine the statistical significance, and so, a p-value of less than or equal to 0.05 would show that there is a statistical significance that was observed and a p-value of greater than 0.05 would show that there was not a statistical significance. FIG. 14 further summarizes the response rates for patients that received RDN under the first definition of orthostatic hypertension.

Figure 15:
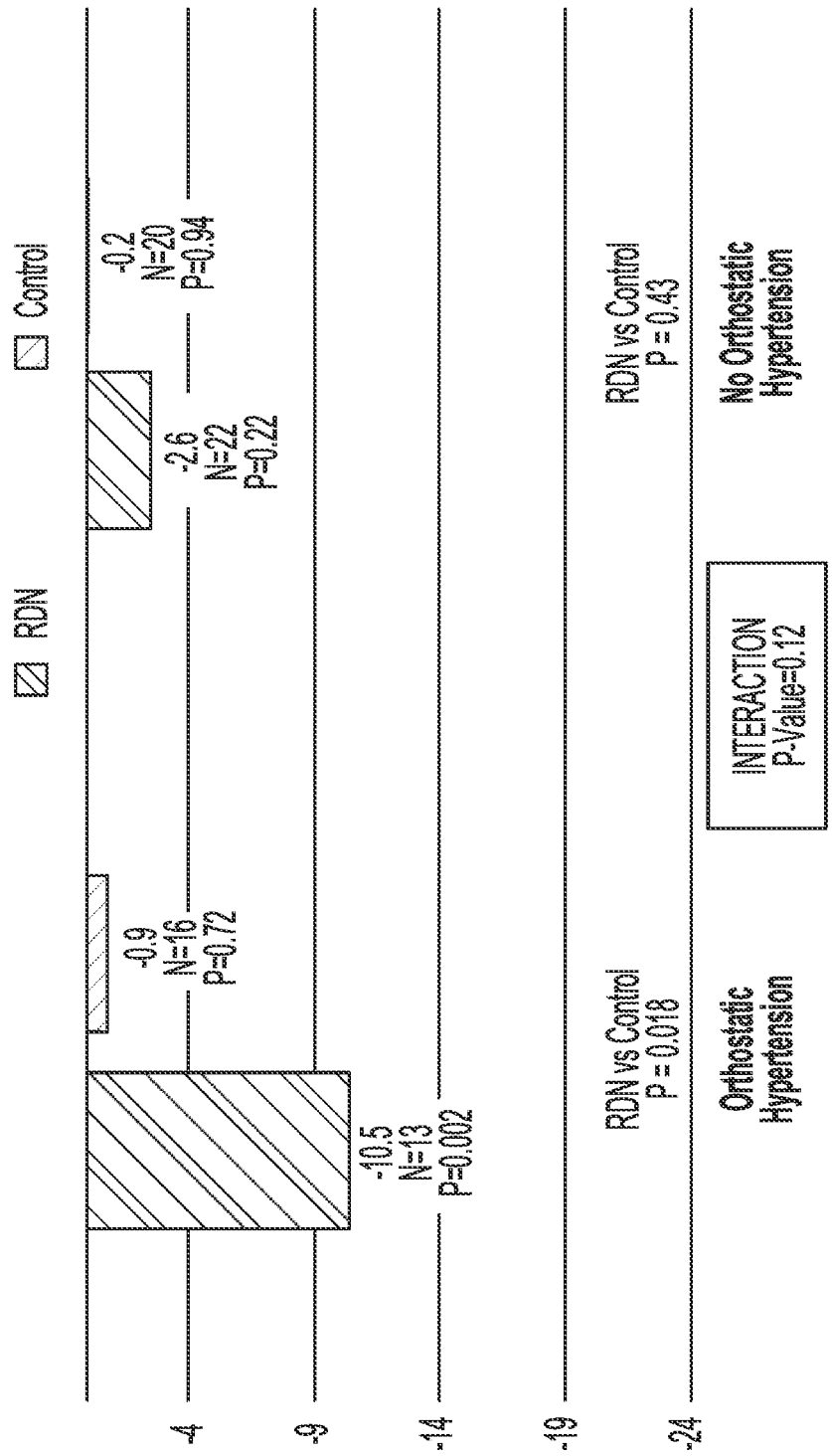
FIG. 15 is a bar chart that shows an example of blood pressure response to renal denervation to off-med patients at 3 months over 24 hours under a second definition of orthostatic hypertension using the therapeutic assembly of FIG. 1 according to an aspect of the invention.

FIGS. 15-19 are bar charts that show the blood pressure response to renal denervation to off-med patients at 3 months under the second definition. FIG. 15 shows the response rates to renal denervation to off-med patients over 24 hours under a second definition of orthostatic hypertension. Similar to FIG. 8, the bar chart shows that among the number, N, subjects that the subjects that had orthostatic hypertension showed a greater change, i.e., decrease in SBP when RDN is performed in comparison to a control group, over the 24 hour period than the subjects that did not have orthostatic hypertension when RDN was performed. Thus, RDN was more effective in decreasing the SBP over the 24 hour period in patients with orthostatic hypertension.

Figure 16:
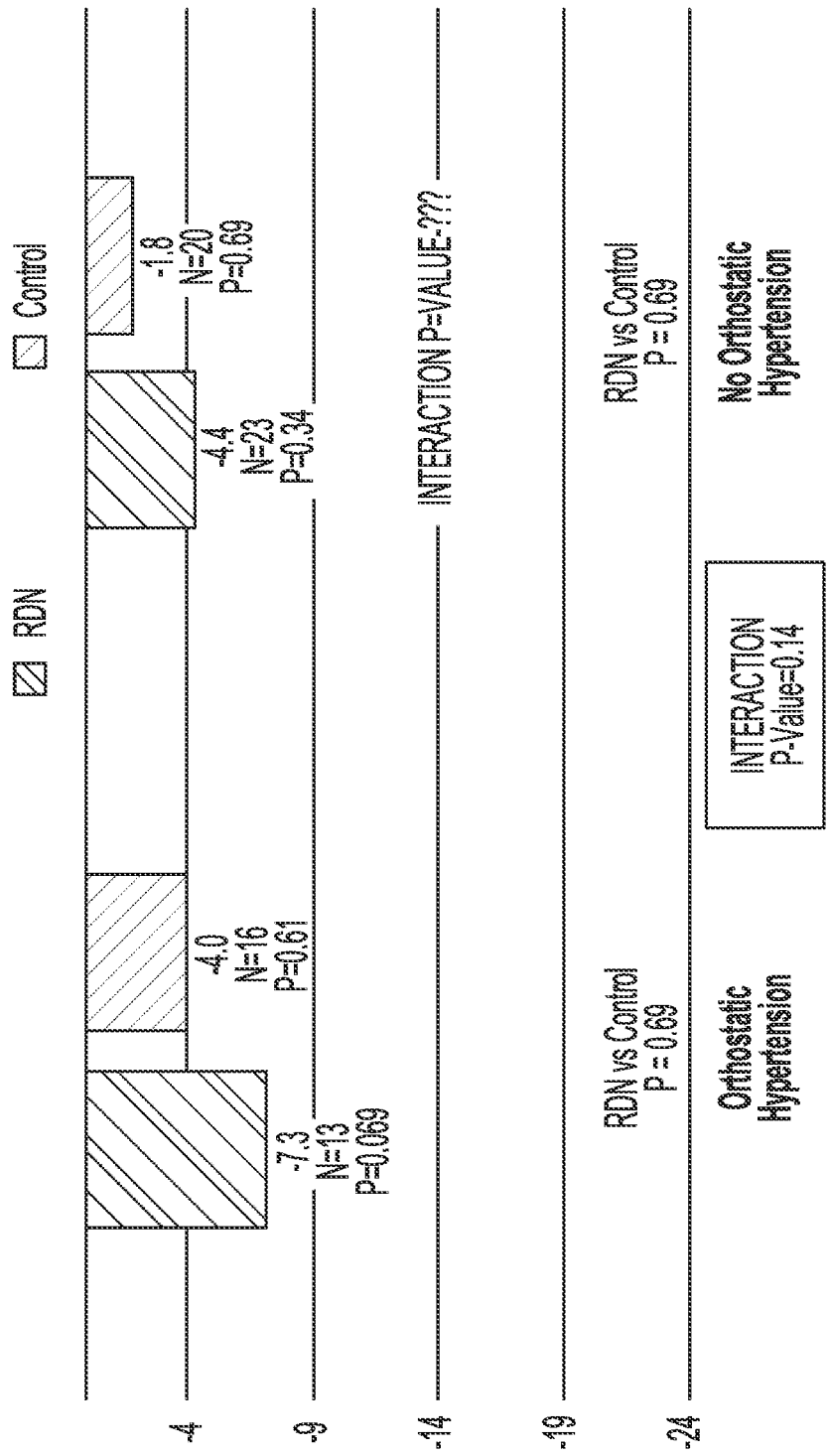
FIG. 16 is a bar chart that shows an example of blood pressure response to renal denervation to off-med patients at 3 months in the morning under a second definition of orthostatic hypertension using the therapeutic assembly of FIG. 1 according to an aspect of the invention.

Similar to FIG. 9, FIG. 16 also shows the subjects that had orthostatic hypertension showed a greater change, i.e., decrease in SBP when RDN is performed in comparison to a control group, over the morning period than the subjects that did not have orthostatic hypertension when RDN was performed. And, FIG. 16 shows that RDN was more effective in decreasing the SBP over the morning period in patients with orthostatic hypertension.

Figure 17:
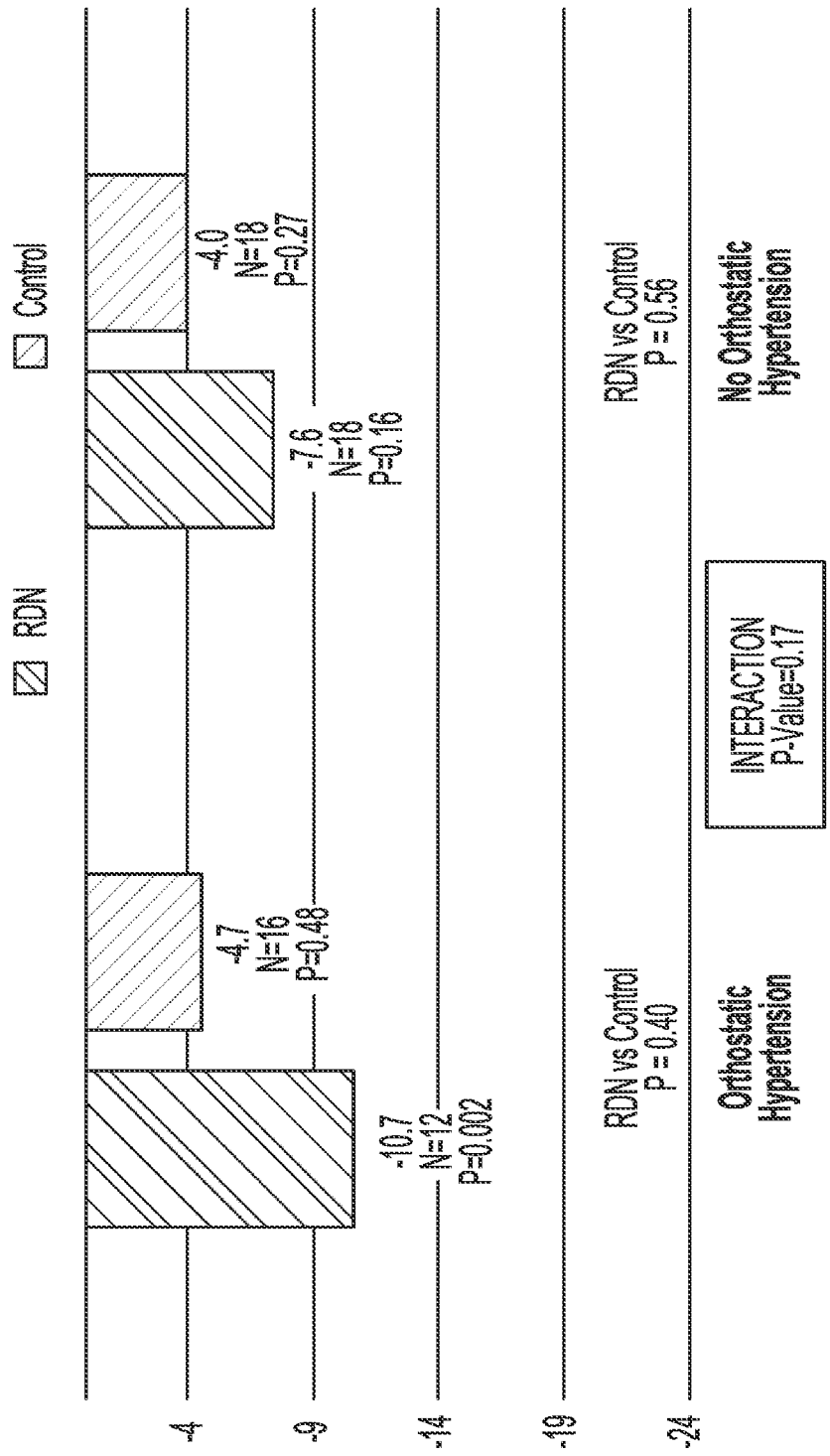
FIG. 17 is a bar chart that shows an example of blood pressure response to renal denervation to off-med patients at 3 months in the peak morning under a second definition of orthostatic hypertension using the therapeutic assembly of FIG. 1 according to an aspect of the invention.
Figure 18:
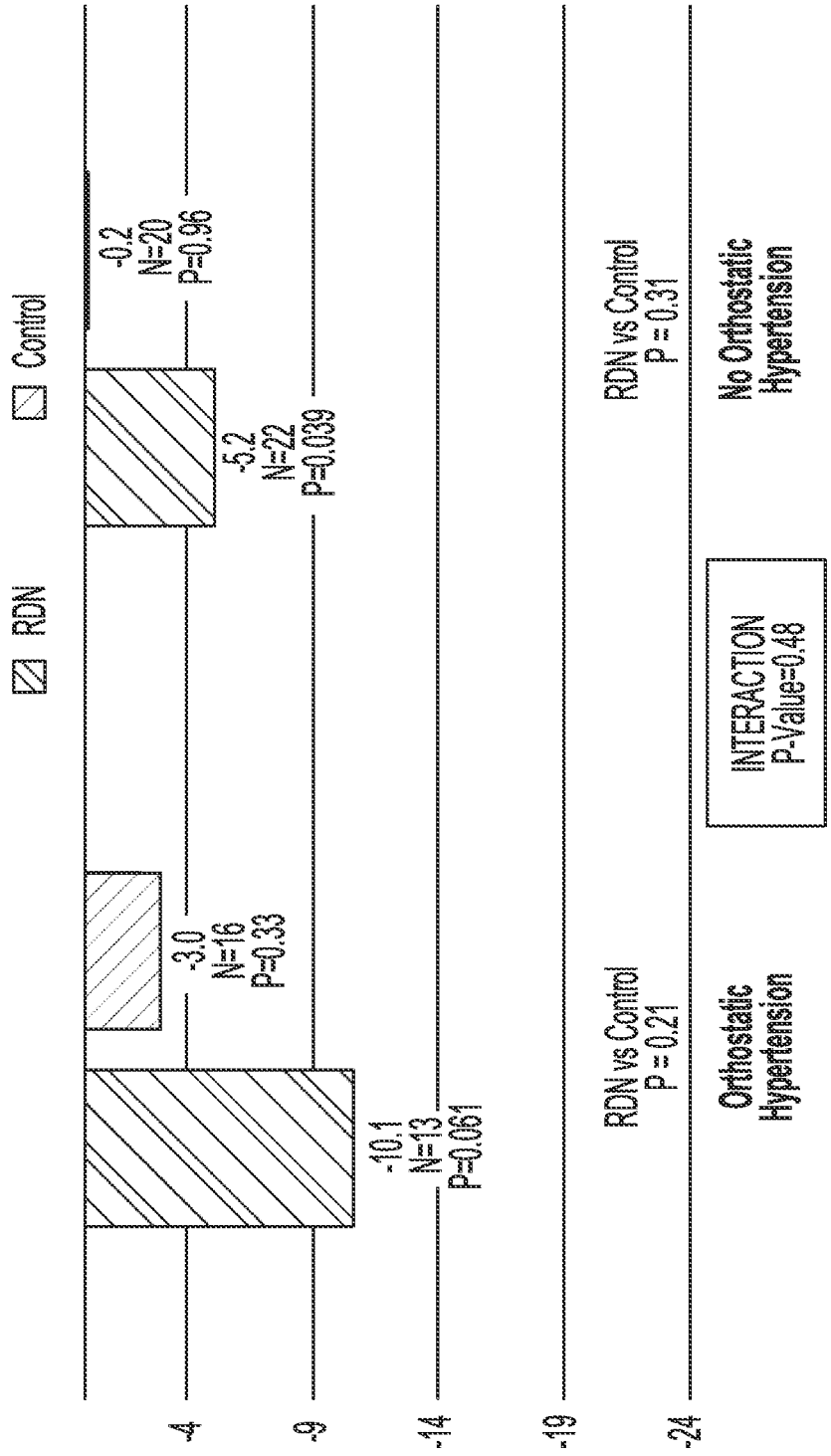
FIG. 18 is a bar chart that shows an example of blood pressure response to renal denervation to off-med patients at 3 months in the nighttime under a second definition of orthostatic hypertension using the therapeutic assembly of FIG. 1 according to an aspect of the invention.
Figure 19:
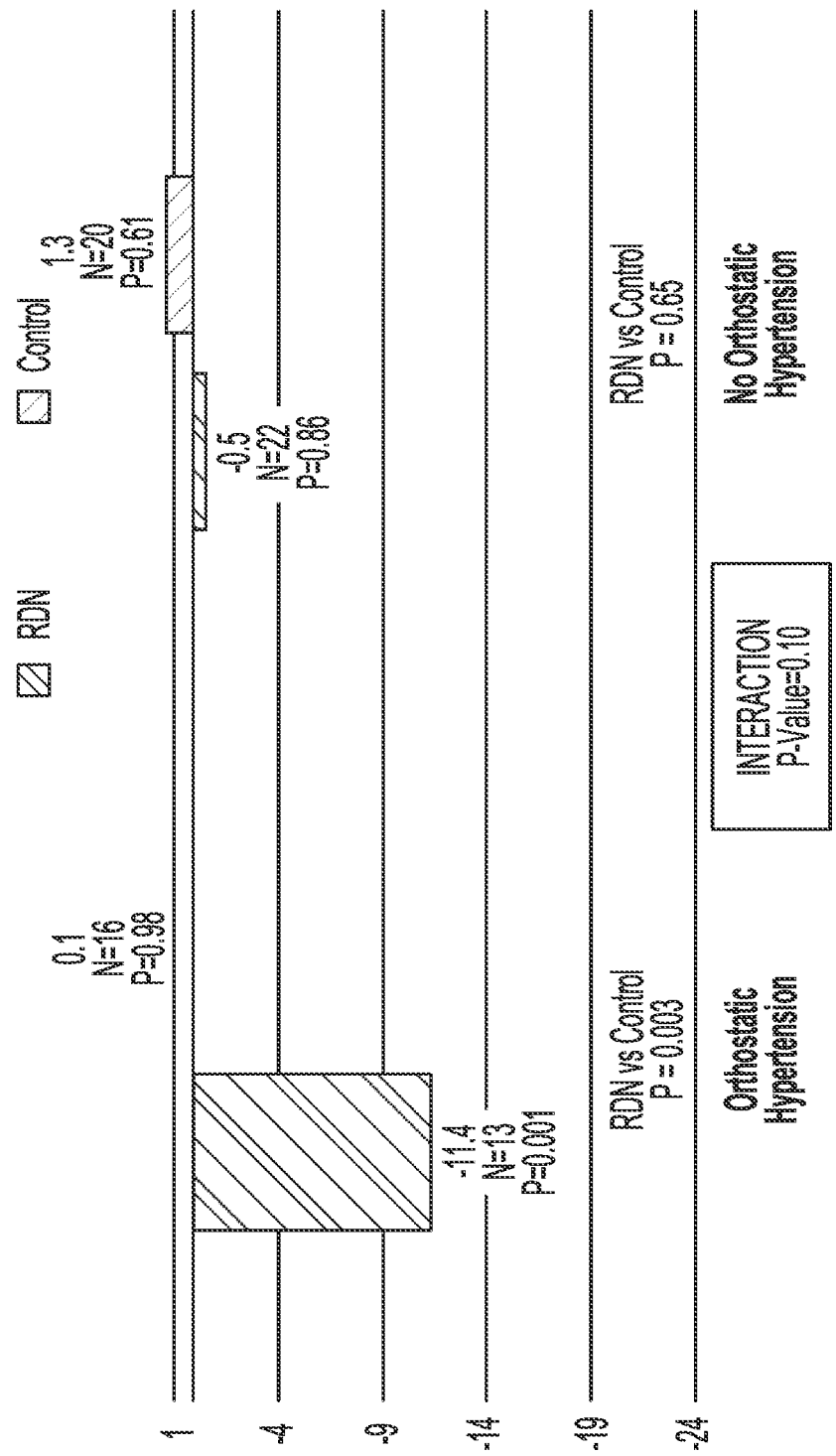
FIG. 19 is a bar chart that shows an example of blood pressure response to renal denervation to off-med patients in the daytime under a second definition of orthostatic hypertension using the therapeutic assembly of FIG. 1 according to an aspect of the invention.

FIGS. 17-19 show the blood pressure responses to renal denervation to off-med patients at 3 months in the peak morning, in the nighttime and in the daytime, respectively, under the second definition. These results demonstrate that RDN is more effective in patients with orthostatic hypertension than in patients with no orthostatic hypertension.

FIG. 20 is a tabular presentation of that summarizes the statistical analysis of the interactions between treatment of orthostatic hypertension patients and non-orthostatic hypertension patients under the second definition of orthostatic hypertension, and FIG. 21 is a table summarizing the blood pressure responses for patients that received RDN under the second definition of orthostatic hypertension. Under the second definition, the p-values of the null hypothesis is further verified in comparison to the p-value of the null hypothesis under the first definition. That is, the null hypothesis that RDN is more effective in orthostatic hypertension patients is further confirmed under the second definition than under the first definition. In particular, the experimental results for the morning, peak morning and nighttime have significant p-values greater than 0.05 under the second definition, and thus, verifying that RDN is more effective in orthostatic hypertension patients during these time periods. Even though FIGS. 8-21 show the effectiveness or responsiveness of renal denervation on patients that are off-medication that have hypertension that is orthostatic, renal denervation is also more effective on patients that have hypertension that is orthostatic when the patients are on one or more medications. The use of renal denervation on patients on one or more medication may reduce the amount or number of medications that the patients are taking.

The blood pressure responses, as shown in FIGS. 8-21, were experimentally taken from an example sample or exploratory group of a small size of patients. In particular, a significant difference is shown between the orthostatic and non-orthostatic hypertension groups in the experimental data for the blood pressure responses over the 24 hour period and during the daytime subgroups. The above analyzed experimental data is solely an example of a small sample size of patients, and so, the use of a larger sample size of patients would show a similar significant difference across all the subgroups.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A method comprising:
   determining that hypertension in a patient is orthostatic;
   predicting an effectiveness of renal denervation therapy on the patient or a responsiveness of the patient to the renal denervation therapy based on determining that the hypertension in the patient is orthostatic; and
   providing the predicted effectiveness or the predicted responsiveness to a clinician.

2. The method of claim 1, wherein determining that the hypertension in the patient is orthostatic includes:
   measuring a standing systolic blood pressure (SBP) of the patient; and
   measuring a supine SBP of the patient.

3. The method of claim 2, wherein determining that the hypertension in the patient is orthostatic further includes:
   determining that the standing systolic blood pressure (SBP) of the patient is greater than the supine SBP by at least 10 mmHg.

4. The method of claim 1, wherein determining that the hypertension in the patient is orthostatic includes:
   measuring a standing diastolic blood pressure (DBP) of the patient; and
   measuring a supine DBP of the patient.

5. The method of claim 4, wherein determining that the hypertension in the patient is orthostatic further includes:
   determining that the standing diastolic blood pressure (DBP) of the patient is greater than the supine DBP by at least 10 mmHg.

6. The method of claim 1, further comprising:
   applying renal denervation therapy to the patient based on the predicted effectiveness or the predicted responsiveness.

7. The method of claim 6, wherein applying renal denervation therapy to the patient comprises:
   determining at least one of a number of ablations or an amount of energy delivered in each ablation of the number of ablations based on the predicted effectiveness or the predicted responsiveness; and
   applying the renal denervation therapy to the patient based on the at least one of the number of ablations or the amount of energy delivered in each ablation.

8. The method of claim 6, wherein applying the renal denervation therapy to the patient includes applying the renal denervation therapy to the patient via at least one of radio frequency (RF) ablation, chemical ablation, cryotherapy, or ultrasound.

9. The method of claim 1, wherein determining that the hypertension in the patient is orthostatic comprises:
   measuring a supine blood pressure of the patient when the patient is in a supine position;
   measuring a standing blood pressure of the patient when the patient in a standing position; and comparing the supine blood pressure to the standing blood pressure to determine whether the hypertension in the patient is orthostatic.

10. The method of claim 9, further comprising:
applying renal denervation therapy to the patient based on determining that the hypertension in the patient is orthostatic,
wherein applying the renal denervation therapy to the patient is based on the hypertension in the patient being orthostatic and a treatment model so that the application of the renal denervation therapy is tailored to the patient.

11. A system comprising:
a user interface; and
a controller configured to:
  determine that hypertension in a patient is orthostatic,
  predict an effectiveness of renal denervation therapy on the patient or a responsiveness of the patient to the renal denervation therapy based on determining that the hypertension in the patient is orthostatic, and
  provide the predicted effectiveness or the predicted responsiveness to a clinician via the user interface.

12. The system of claim 11, further comprising a therapeutic assembly configured to deliver renal denervation therapy to the patient, wherein the controller is configured to control delivery of the renal denervation therapy to the patient by the therapeutic assembly based on the predicted effectiveness or the predicted responsiveness.

13. The system of claim 12, wherein the controller is configured to control delivery of renal denervation therapy to the patient based on a treatment model so that the application of the renal denervation therapy is tailored to the patient.

14. The system of claim 12, wherein the controller is configured to control delivery of renal denervation therapy to the patient by at least:
  determining at least one of a number of ablations or an amount of energy delivered in each ablation of the number of ablations based on the predicted effectiveness or the predicted responsiveness, and
  controlling the delivery of the renal denervation therapy to the patient based on the at least one of the number of ablations or the amount of energy delivered in each ablation.

15. The system of claim 11, further comprising:
a first sensor configured to detect a position of the patient; and
a second sensor configured to detect a blood pressure of the patient,
wherein, to determine that the hypertension in the patient is orthostatic, the controller is configured to:
  determine, using the first sensor, that the patient is in a supine position based on the detected position of the patient,
  determine, using the second sensor, a supine blood pressure of the patient when the patient is in the supine position,
  determine, using the first sensor, that the patient is in a standing position based on the detected position of the patient,
  determine, using the second sensor, a standing blood pressure of the patient when the patient in the standing position, and
  compare the supine blood pressure to the standing blood pressure to determine whether the hypertension in the patient is orthostatic.

16. The system of claim 11, wherein to determine that the hypertension in the patient is orthostatic the controller is configured to determine that a standing systolic blood pressure (SBP) is greater than a supine SBP by at least 10 mmHg or that a standing diastolic blood pressure (DBP) of the patient is greater than the supine DBP by at least 10 mmHg.

17. The system of claim 11, wherein to determine that the hypertension in the patient is orthostatic, the controller is configured to determine that a standing systolic blood pressure (SBP) is greater than a supine SBP by at least 20 mmHg or that a standing diastolic blood pressure (DBP) of the patient is greater than the supine DBP by at least 20 mmHg.

18. The system of claim 11, wherein to predict the effectiveness or the responsiveness of application of the renal denervation therapy to the patient based on determining that the hypertension in the patient is orthostatic, the controller is configured to:
  predict the effectiveness or the responsiveness of application of the renal denervation therapy to the patient using a treatment model prior to applying the renal denervation therapy.

19. A system comprising:
a therapeutic assembly configured to deliver renal denervation therapy to a patient; and
a controller configured to:
  determine that hypertension in the patient is orthostatic,
  predict an effectiveness of renal denervation therapy on the patient or a responsiveness of the patient to the renal denervation therapy based on determining that the hypertension in the patient is orthostatic, and
  control delivery of the renal denervation therapy to the patient by the therapeutic assembly based on the predicted effectiveness or the predicted responsiveness.

20. The system of claim 19, wherein the controller is further configured to:
  provide the predicted effectiveness or the predicted responsiveness to a clinician.

* * * * *